US007498150B2

(12) United States Patent
Nelson et al.

(10) Patent No.: US 7,498,150 B2
(45) Date of Patent: Mar. 3, 2009

(54) MATERIALS AND METHODS TO INCREASE PEPTIDE CHAIN EXPRESSION

(75) Inventors: Pamela H. Nelson, Downingtown, PA (US); Gordon Moore, Wayne, PA (US); Barry A. Morse, Havertown, PA (US); Haimanti Dorai, Exton, PA (US); Bernard Scallon, Wayne, PA (US); Linda Hendricks, Lansdale, PA (US)

(73) Assignee: Centocor, Inc., Malvern, PA (US)

( * ) Notice: Subject to any disclaimer, the term of this patent is extended or adjusted under 35 U.S.C. 154(b) by 315 days.

(21) Appl. No.: 11/503,103

(22) Filed: Aug. 11, 2006

(65) Prior Publication Data

US 2008/0213829 A1 Sep. 4, 2008

Related U.S. Application Data

(60) Provisional application No. 60/707,564, filed on Aug. 11, 2005.

(51) Int. Cl.
*C12P 21/06* (2006.01)
*C12N 1/20* (2006.01)
*C07H 21/02* (2006.01)

(52) U.S. Cl. .................. 435/69.1; 435/252.3; 536/23.1

(58) Field of Classification Search ................ 435/69.1, 435/252.3; 536/23.2

See application file for complete search history.

(56) References Cited

U.S. PATENT DOCUMENTS 7,129,062 B2 10/2006 Mermod et al.

OTHER PUBLICATIONS

GenBank Accession No. AC102853, Aug. 21. 2002.
GenBank Accession No. AC132331, May 15, 2004.
PCT International Search Report dated Sep. 25, 2007.
Harris, et al., "Forced MyHCIIB Expression Following Targeted Genetic Manipulation of Conditionally Immortalized Muscle Precursor Cells," Experimental Cell Research, 253:523-532 (1999).
Matz, et al., "Fluorescent proteins from nonbioluminescent Anthozoa species," Nature Biotechnology, 17:969-973 (1999).
Yusufzai, et al., "The 5'-HS4 chicken {beta}-globin insulator is a CTCF-dependent nuclear matrix-associated element," PNAS: 101: 8620-8624 (2004).
Furth, et al., "The variability in activity of the universally expressed human cytomegalovirus immediate early gene 1 enhancer/promoter in transgenic mice," Nucleic Acids Research, 19(22): 6205-6208 (1991).
GenBank Accession No. CAAA01060907, The Mouse Genome Sequencing Consortium, May 2, 2002.
GenBank Accession No. CAA01122220, The Mouse Genome Sequencing Consortium, May 2, 2002.
ATCC® No. CRL-1573™.
ATCC® No. CRL-9618™.
ATCC® No. CRL-1581™.

*Primary Examiner*—Tekchand Saidha
(74) *Attorney, Agent, or Firm*—Kirk Baumeister

(57) ABSTRACT

DNA sequences that increase peptide chain expression when operably linked to a gene encoding the peptide chain and methods of generating a peptide chain expression host cell using the foregoing are disclosed. Peptide chain expression host cells are also disclosed.

20 Claims, 11 Drawing Sheets

Ligation Mediated PCR

Chromosome 12 Flanking Sequence

Chromosome 6 Flanking Sequence

DV-BASE

Median Fluorescence = 142

DV-6

Median Fluorescence = 410

DV-12

Median Fluorescence = 273

DV-6/12

Median Fluorescence = 395

DVbase w/o G418
~81% cells very high expression
Median fluorescence 547.37

DVbase + G418
~94% cells very high expression
Median fluorescence 1084.32

DV6/12 w/o G418
~81% cells very high expression
Median fluorescence 1321.58

DV6/12 + G418
~98% cells very high expression
Median fluorescence 2186.97

(A)

(B)

(C)

12R Fragments

SEQUENCE LISTING

```
<160> NUMBER OF SEQ ID NOS: 8

<210> SEQ ID NO 1
<211> LENGTH: 4152
<212> TYPE: DNA
<213> ORGANISM: Mus musculus strain BALB/c

<400> SEQUENCE: 1

cagttactca cagggccagc cagcaacaca gttcaaagct tgtgagtgat gatgtgacat     60

gtgtctatga gagggagaag cctgctgtga tgacaggacc caagctactg caacagagag    120
```

-continued

```
gtgggaatgt ccctcagatc tgaggaaacc aaagaatctg gtagttacac cttagtctta    180

aacatctcca gaatgaaatt ctcagctgac atttgtagat aattctggag gtaaaagaaa    240

tgctaaccta agtgatgaag tccatagcag atccatcaat cagcagatct tatatatcag    300

acagatacca aagagctgca atgcacctta agaaatccca aataggccaa gtgaaaaaca    360

tacaaaagcc ccttttaact acattcagag caagtagatt gagttgaggg acagaagctg    420

acactggtgg gtgagaaaaa gttcaaaata tagctgagca aatgccccat aaaactgttt    480

aaaagaataa taagtgagtg ctaatagccc actagttaat cccagtgtga agcagaggca    540

gaggcagagg cagaggcaga ggcagaggca gaggcagagg cagaggcaga ggcagaggca    600

gaggcaaatc tctgtgtgtg aggccggcct attctatgga gcaagttcca agacagccaa    660

ggctgagaga caaaccctgt ctctgaatga atgaatagat agatagatag atagatagat    720

agatagatag atagataaga tagataaagt ctgtaagcaa gatcacaaac acagaggtca    780

gaagagggca tcagcatctt cccatatcac tcttaatcta ttcctgtgag gcaaggcctc    840

tccctggacc ttgggcccac attccacaga tagactggaa gcaggaagcc acagctttgc    900

ttagatctgg gattacaggg gtataaggaa tcacagcttg gtaggtaggt gctgggatct    960

ggcatgatgg cacagcagct gtccttttcc atggagatac ttccccagcc taagagggtt   1020

tcttaagcct gctcatcata aactgtctgg gggaaggaga accctatggg gggggggcgg   1080

gggggaagac agaatctttt ggaaagaagt ttagtcatca gcgtttcttc taagtgccaa   1140

atgacatttt tataagcaag tttgatagaa ccatagtgca attcaagcac tttgaactgg   1200

acagactcca agacctgtgg gaacttagcc cagaatcctg gaaaaggggg agccatgata   1260

agacacctga aagcaggaaa aactttgatt ttcagaaaag taagtcctat aaactggtaa   1320

gtttaacacc atcgacctgt gaaatttaaa actgatctca tggatctgct aatgtgcagg   1380

catgtgaaag tcaaaggctc acaaatgtcc aagcatggta aagacaaaaa ctggcttgca   1440

gattagcctt ttcctggtag acatggtcac tgaatagcat catgtctagt atgcttatat   1500

tgaaggacta gagtcctaag ggttgaaatg acatactggc agaccatggt cagtccacat   1560

ttacctagtg ttattttaaa gctcgaagag gctgtgcctg agtgcatact ttgcactgta   1620

tagaatcccc acagagcacc tcctgtgtct gtctctaggt ttggttgcag ccatccctgc   1680

ctttttgca tatcaatatc ttggattttt ggaaagcaga attctatgtc ataaacaccc   1740

agagtgcctg agaggctgca aagctcttaa aaacaggagt atggcccaaa tcaaatcaaa   1800

gaatatttag tatggatagt tatataaatt aaaggtcaga gcactgtaga gacagaatgg   1860

taagatattt gatgtaggag aggaaacaaa acaaaacaaa accaaagtca gctccaagcc   1920

tagaatccta agttaagaac agtataacag aaacaaaacc tggcgtgtag acacatcagt   1980

caacacagag ttgagagtgc taaggtaaac tcttaagatt atggtcagct agggactcag   2040

aataaatgaa tcttcacatg ccaattgacg ctagccacca caccacatac aaaacatgca   2100

ctgaacatgg atgcagatct aaagaattac taaacccagc agatatgtcc aagcttttct   2160

gacattgctc tgacagtgca atcttatcca atggtacact cacactacag gtcgaacgtg   2220

cctgcatcaa cttttaaaat gaaaacacag ggaaaaaaaa cctcaggtct aatactcagg   2280

tctaataaaa atagcacaat ccacaagggg aaaattgtta caccaaactg cattattcag   2340

cccttaactt caaatttcat ttctaaaata aacagaagtg ccagaatagg agacattctc   2400

aagttataca tcttataaga cttgttacaa gaataccgag ctgataagaa tagttaaaac   2460

atgataccca aaaggcagaa aagtgacccc aaatacataa aactcttact aagtgagcag   2520
```

-continued

```
aaagacagac aacctggttt aaaaataggc aaaattgagt atccttgtca gcaaagacaa   2580

acacaccaaa ggtcttcact atccagtcac caggaaggtc ggattaaaat catggcaggg   2640

agccttctca tcatctagta tggcaaccgt tctgataaga tgtggaaaaa agtggaatgc   2700

gcaacactct gcacacaggc acaggaaaga gcaaagccac tttgggggaa aaaagggcaa   2760

aaagccacaa acagtagcaa cggaaaacca aaccaaaagc cccaaaaaca aacaaacaaa   2820

caaacaaaca aacaagccca aaaagggctg gaaacagtga gtggtgtatg cctttaaggc   2880

aggggcaggc agatctctga gttcaaggcc aacctggtcc acagagttcc aaggtagcca   2940

gggctacaca gagaaacact gtctcaaaaa gaaaaaaaac caataaatga ctgagtgaat   3000

gaataagtga gttaaaaaaa agtttctaaa aacattaaaa aaaatcacaa accatttcac   3060

acttaaaaga aatgaaaatg cttacataaa actcctagac aaatggtcat agtttagttg   3120

tattccaaca actaaaaaca atctaaaggc aggtgtggta gggaatgcct ttgatcccaa   3180

ctctcaggag gcagaggtag atgtagctct gtcagtttga ggttagccta gtctacgaat   3240

cgtgttacag aacagccagg aatacacaga aacccgtctc aaaaaaaaaa aaaaaaaaaa   3300

aagagaaaaa ttaaaaagaa aaataaaaac aaagaaaaat acaattcaaa tatccactaa   3360

tagacacaat gtgataaaca cccacataat caactactac tcagcaggaa gaggaaatac   3420

tgaaagcaca tcacatgggt aaacactgaa aacactgaag caaacaagtc atctgcaaaa   3480

ggctgtatca tcagtgacta tgtgaactgt gcagaacaga caggctaagg gttccagaag   3540

ctgaaaataa ggaatgactg actataaata aacagacact ctaaaggtgg gagagctgag   3600

gactgcacaa ctcactcgca ctagacactt aacactgctg cctctgctga gtctgaggcc   3660

tgggaacaag agtggggcgc acacagaatg ctcaggctac atcagttctc agggttcact   3720

aggctgtatt accagctcaa gagagactca acaaaaagac ttcaagtggt gagtgtggca   3780

atgaagatag gagcttgatg gtgtaggttg taaaagtgtt ttagcctata aatgtggcaa   3840

acgattcctt catgcttagt tcagagatcc aactttcaaa gtctgatgtc cacaaacaga   3900

tccccaagaa ggctgctgta tttgagaaag gaagtggaaa gttcttccat acagtatgtg   3960

tgaggaatgg ttagaatgga tacctagaga aaaagatctt gtgacctaag cgacctaagg   4020

tcactaagaa aaagcgacct atttcccatg ccagaattca gaaaggaaat ggctctttgc   4080

aatcttaata gtgaaaactg ttgctactta gggactaaga catatgcact ggtctccgga   4140

tctgctgaag ca                                                        4152
```

<210> SEQ ID NO 2
<211> LENGTH: 2304
<212> TYPE: DNA
<213> ORGANISM: Mus musculus strain BALB/c

<400> SEQUENCE: 2

```
gtgcattctt tccttggttg atggctggcc actgtgcata tatcgcaaag ctcggaagac     60

ctgactagac acttgacaga gcttagctta attgaaaatt cagttccctc ccctttttaa    120

attgaaagaa catttttatt ttgttgctgt ttcgattttg ttttgtttga gccatagtga    180

ggattaaact ttggtcttcg cgcttgcaaa gcaagcacac ttccagctga gctgtattct    240

acccagaact cagccatgtg tgcagcttca cagggtcacc ggctccctcc ctgcttcagc    300

cttaggattc tcctgtctca gcctagtgtg tgattggaga tgtccaccat cacactctgt    360

tagtccgtct tggtttctgt aagagattgc atccccaatg gtgatgtcca gttgacaaca    420
```

-continued

```
gtaaacgcct tgtagaggta ggttactgtt gtatgttgta tcatgcctgg tacctctcct    480

ccgggcttta gcctgtatgt gtttctcctg ggcgtagagg agactttaaa tcacaagtgc    540

agggaggcgg ctcagtcttc actaagaaga ctgcctgctt ggtgtgcaca aggttcagga    600

tttagcctcc gcactggaaa gcaatcagct ggccgattga ttaattcaag agcagtcttt    660

aagaagcagg ccgtctgctg tctgctgcct gctgcctgct gcctgctgcc tgctgcctgc    720

tgcctgctgc ctgctgcctg ctgcctgctg cctgctgcct gctgcctgct gtctgctgtc    780

tgctgtctgc tgcctgctgc ctgctgcctg ctgcctgctg tctgtctgga cttgccagct    840

gaaatagaaa gggacttgtc ttctttagag tctttgtgcc cttgtctctg ttgagctggg    900

cagccttctc cagtgactgt ccagacccaa gaaacgaatt gactgatcca tttccagaca    960

gctagcaata gcaacatcaa gtgtgaagac actagtagat tcaatgtaga tacttgtttt   1020

tgtaaacaaa ataaaaatat tttaaataaa aaagtttaaa ggaaataaat ctatgacaac   1080

tgtcagaaca ggactttgcc ctaaggaatc gtgcttaaaa taaatcccct tctgccggca   1140

gtctagacac ttgttacaca ccagatccat gaaacttagt agatacctaa atagatgaag   1200

tctcaggcag ttaacctctt aagtatgagg tgtacatgct agtgaattta atgtacattt   1260

atttattttt ttatttccta gggctgataa agatagcttt tcagtttgag aattctcttt   1320

ttttcccatc ctgttgcata aatatcctgg aaaggaacgg tcctaagaac aagaatgtgt   1380

ccttaaaata cacatccaat ctgctttatt atctctcttt ctctctctct ctctctctct   1440

ctctctctct ctctctctct ctctctgtgt gtgtgtgtgt gtgtgtgtgt gtgtgtgtgt   1500

gtgtgtgtgt gtgtgtgtgt gtgtgtgtac agtgcacatg tttgcattgg aatgtgtagt   1560

ggtcagagga ccaccctcag atcagaagta gattctccca ctgtgtaggt tcctggcatc   1620

agctcaggtt actaggcttg cacagcaagc accctttact tgctaagcca cttcactgcc   1680

tttattctgt tctgttctgt tctgttctgt tttgttttgt tttgtttgtt gttgttgttg   1740

gtggtgtggt tcttgttttt gtttttgttt ttgtttttgt ttttgaagca aggttttctg   1800

gaatccaggc tatctttgaa cgcctgctcc tcctgccccc atctcctgag tgctgggata   1860

cagttgtgtg ccatcatgtc cagcttgtgc atcgttggag attagtatca gggctttttg   1920

catgctgggc atccccaatg gtgatttacc agttgaggca catgcagtcc cagcccagat   1980

atcttcgtaa gtactaagct aaatatgtat gctttcttaa accaagaaat agccatatac   2040

ttcagtatgt aagccattct tacaaacatg atgagaattt atataaacaa aaggttccag   2100

gagtatacag aatacaccta aagcattgct aataggtttt ggaaaaccaa tctaatgttc   2160

aggaagatta cttgtgacaa cttgtaggga agctttactg agcaatggtt tatagaccat   2220

ctttctctct gtctcttgag gtaattttgc actttgtctc gttctaggaa tataccatgc   2280

tgtgtctgtt gtgtggcaaa gctg                                          2304
```

<210> SEQ ID NO 3
<211> LENGTH: 473
<212> TYPE: DNA
<213> ORGANISM: Mus musculus strain BALB/c

<400> SEQUENCE: 3

```
gtgcattctt tccttggttg atggctggcc actgtgcata tatcgcaaag ctcggaagac     60

ctgactagac acttgacaga gcttagctta attgaaaatt cagttccctc cccttttttaa   120

attgaaagaa catttttatt ttgttgctgt ttcgattttg ttttgtttga gccatagtga    180

ggattaaact ttggtcttcg cgcttgcaaa gcaagcacac ttccagctga gctgtattct    240
```

```
acccagaact cagccatgtg tgcagcttca cagggtcacc ggctccctcc ctgcttcagc    300

cttaggattc tcctgtctca gcctagtgtg tgattggaga tgtccaccat cacactctgt    360

tagtccgtct tggtttctgt aagagattgc atccccaatg gtgatgtcca gttgacaaca    420

gtaaacgcct tgtagaggta ggttactgtt gtatgttgta tcatgcctgg tac           473


<210> SEQ ID NO 4
<211> LENGTH: 677
<212> TYPE: DNA
<213> ORGANISM: Mus musculus strain BALB/c

<400> SEQUENCE: 4

gtacctctcc tccgggcttt agcctgtatg tgtttctcct gggcgtagag gagactttaa     60

atcacaagtg cagggaggcg gctcagtctt cactaagaag actgcctgct tggtgtgcac    120

aaggttcagg atttagcctc cgcactggaa agcaatcagc tggccgattg attaattcaa    180

gagcagtctt taagaagcag gccgtctgct gtctgctgcc tgctgcctgc tgcctgctgc    240

ctgctgcctg ctgcctgctg cctgctgcct gctgcctgct gcctgctgcc tgctgcctgc    300

tgtctgctgt ctgctgtctg ctgcctgctg cctgctgcct gctgcctgct gtctgtctgg    360

acttgccagc tgaaatagaa agggacttgt cttctttaga gtctttgtgc ccttgtctct    420

gttgagctgg gcagccttct ccagtgactg tccagaccca agaaacgaat tgactgatcc    480

atttccagac agctagcaat agcaacatca agtgtgaaga cactagtaga ttcaatgtag    540

atacttgttt ttgtaaacaa aataaaaata ttttaaataa aaaagtttaa aggaaataaa    600

tctatgacaa ctgtcagaac aggactttgc cctaaggaat cgtgcttaaa ataaatcccc    660

ttctgccggc agtctag                                                   677


<210> SEQ ID NO 5
<211> LENGTH: 782
<212> TYPE: DNA
<213> ORGANISM: Mus musculus strain BALB/c

<400> SEQUENCE: 5

ctagacactt gttacacacc agatccatga aacttagtag atacctaaat agatgaagtc     60

tcaggcagtt aacctcttaa gtatgaggtg tacatgctag tgaatttaat gtacatttat    120

ttattttttt atttcctagg gctgataaag atagcttttc agtttgagaa ttctcttttt    180

ttcccatcct gttgcataaa tatcctggaa aggaacggtc ctaagaacaa gaatgtgtcc    240

ttaaaataca catccaatct gctttattat ctctctttct ctctctctct ctctctctct    300

ctctctctct ctctctctct ctctgtgtgt gtgtgtgtgt gtgtgtgtgt gtgtgtgtgt    360

gtgtgtgtgt gtgtgtgtgt gtgtgtacag tgcacatgtt tgcattggaa tgtgtagtgg    420

tcagaggacc accctcagat cagaagtaga ttctcccact gtgtaggttc ctggcatcag    480

ctcaggttac taggcttgca cagcaagcac cctttacttg ctaagccact tcactgcctt    540

tattctgttc tgttctgttc tgttctgttt tgttttgttt tgtttgttgt tgttgttggt    600

ggtgtggttc ttgtttttgt ttttgttttt gtttttgttt ttgaagcaag gttttctgga    660

atccaggcta tctttgaacg cctgctcctc ctgcccccat ctcctgagtg ctgggataca    720

gttgtgtgcc atcatgtcca gcttgtgcat cgttggagat tagtatcagg gctttttgca    780

tg                                                                   782


<210> SEQ ID NO 6
```

```
<211> LENGTH: 384
<212> TYPE: DNA
<213> ORGANISM: Mus musculus strain BALB/c

<400> SEQUENCE: 6

catgctgggc atccccaatg gtgatttacc agttgaggca catgcagtcc cagcccagat     60

atcttcgtaa gtactaagct aaatatgtat gctttcttaa accaagaaat agccatatac    120

ttcagtatgt aagccattct tacaaacatg atgagaattt atataaacaa aaggttccag    180

gagtatacag aatacaccta aagcattgct aataggtttt ggaaaaccaa tctaatgttc    240

aggaagatta cttgtgacaa cttgtaggga agctttactg agcaatggtt tatagaccat    300

ctttctctct gtctcttgag gtaattttgc actttgtctc gttctaggaa tataccatgc    360

tgtgtctgtt gtgtggcaaa gctg                                           384


<210> SEQ ID NO 7
<211> LENGTH: 1146
<212> TYPE: DNA
<213> ORGANISM: Mus musculus strain BALB/c

<400> SEQUENCE: 7

gtgcattctt tccttggttg atggctggcc actgtgcata tatcgcaaag ctcggaagac     60

ctgactagac acttgacaga gcttagctta attgaaaatt cagttccctc ccctttttaa    120

attgaaagaa catttttatt ttgttgctgt ttcgattttg ttttgtttga gccatagtga    180

ggattaaact ttggtcttcg cgcttgcaaa gcaagcacac ttccagctga gctgtattct    240

acccagaact cagccatgtg tgcagcttca cagggtcacc ggctccctcc ctgcttcagc    300

cttaggattc tcctgtctca gcctagtgtg tgattggaga tgtccaccat cacactctgt    360

tagtccgtct tggtttctgt aagagattgc atccccaatg gtgatgtcca gttgacaaca    420

gtaaacgcct tgtagaggta ggttactgtt gtatgttgta tcatgcctgg tacctctcct    480

ccgggcttta gcctgtatgt gtttctcctg ggcgtagagg agactttaaa tcacaagtgc    540

agggaggcgg ctcagtcttc actaagaaga ctgcctgctt ggtgtgcaca aggttcagga    600

tttagcctcc gcactggaaa gcaatcagct ggccgattga ttaattcaag agcagtcttt    660

aagaagcagg ccgtctgctg tctgctgcct gctgcctgct gcctgctgcc tgctgcctgc    720

tgcctgctgc ctgctgcctg ctgcctgctg cctgctgcct gctgcctgct gtctgctgtc    780

tgctgtctgc tgcctgctgc ctgctgcctg ctgcctgctg tctgtctgga cttgccagct    840

gaaatagaaa gggacttgtc ttctttagag tctttgtgcc cttgtctctg ttgagctggg    900

cagccttctc cagtgactgt ccagacccaa gaaacgaatt gactgatcca tttccagaca    960

gctagcaata gcaacatcaa gtgtgaagac actagtagat tcaatgtaga tacttgtttt   1020

tgtaaacaaa ataaaaatat tttaaataaa aaagtttaaa ggaaataaat ctatgacaac   1080

tgtcagaaca ggactttgcc ctaaggaatc gtgcttaaaa taaatcccct tctgccggca   1140

gtctag                                                              1146


<210> SEQ ID NO 8
<211> LENGTH: 1162
<212> TYPE: DNA
<213> ORGANISM: Mus musculus strain BALB/c

<400> SEQUENCE: 8

ctagacactt gttacacacc agatccatga aacttagtag atacctaaat agatgaagtc     60

tcaggcagtt aacctcttaa gtatgaggtg tacatgctag tgaatttaat gtacatttat    120
```

-continued

```
ttatttttt atttcctagg gctgataaag atagcttttc agtttgagaa ttctcttttt    180
ttcccatcct gttgcataaa tatcctggaa aggaacggtc ctaagaacaa gaatgtgtcc    240
ttaaaataca catccaatct gctttattat ctctctttct ctctctctct ctctctctct    300
ctctctctct ctctctctct ctctgtgtgt gtgtgtgtgt gtgtgtgtgt gtgtgtgtgt    360
gtgtgtgtgt gtgtgtgtgt gtgtgtacag tgcacatgtt tgcattggaa tgtgtagtgg    420
tcagaggacc accctcagat cagaagtaga ttctcccact gtgtaggttc ctggcatcag    480
ctcaggttac taggcttgca cagcaagcac cctttacttg ctaagccact tcactgcctt    540
tattctgttc tgttctgttc tgttctgttt tgttttgttt tgtttgttgt tgttgttggt    600
ggtgtggttc ttgtttttgt ttttgttttt gtttttgttt ttgaagcaag gttttctgga    660
atccaggcta tctttgaacg cctgctcctc ctgcccccat ctcctgagtg ctgggataca    720
gttgtgtgcc atcatgtcca gcttgtgcat cgttggagat tagtatcagg gctttttgca    780
tgctgggcat ccccaatggt gatttaccag ttgaggcaca tgcagtccca gcccagatat    840
cttcgtaagt actaagctaa atatgtatgc tttcttaaac caagaaatag ccatatactt    900
cagtatgtaa gccattctta caaacatgat gagaatttat ataaacaaaa ggttccagga    960
gtatacagaa tacacctaaa gcattgctaa taggttttgg aaaaccaatc taatgttcag   1020
gaagattact tgtgacaact tgtagggaag ctttactgag caatggttta tagaccatct   1080
ttctctctgt ctcttgaggt aattttgcac tttgtctcgt tctaggaata taccatgctg   1140
tgtctgttgt gtggcaaagc tg                                            1162
```

MATERIALS AND METHODS TO INCREASE PEPTIDE CHAIN EXPRESSION

CROSS-REFERENCE TO RELATED APPLICATIONS

This application claims the benefit of U.S. Provisional Application Ser. No. 60/707,564, filed 11 Aug. 2005, the entire contents of which is incorporated herein by reference.

FIELD OF THE INVENTION

The present invention relates to DNA sequences that increase peptide chain expression when operably linked to a gene encoding the peptide chain and methods of generating a peptide chain expression host cell using the forgoing. The invention also relates to peptide chain expression host cells.

BACKGROUND OF THE INVENTION

Large-scale production of recombinant proteins, such as antibodies, typically relies on expression of the protein from a cultured production cell line. Proteins expressed by cultured cells can be readily recovered and purified using standard bench or industrial-scale purification techniques.

Antibody-producing cell lines can be created by random integration of heavy chain and light chain antibody expression constructs into host cell genomic DNA. This random integration yields a high percentage of stable clones having relatively low levels of antibody expression. This phenomenon may be due to the fact that many integrations insert transgenes into areas of condensed chromatin, which are not conducive to high levels of expression (Furth et al., *Nucl. Acids. Res.,* 19, 6205-6208 (1991)).

Protein expression level is an important parameter affecting the production and purification of such proteins from a bioreactor or other system. In general, higher purified protein yields can be attained when the expression level is relatively high. Conversely, if the expression level is low, yields may be low and protein purification may not be economically feasible.

One approach to circumventing the problem of cells with low protein expression has been to subclone and isolate high expressing cells from a population of low expressing cells. Typically, this requires several time and labor-intensive rounds of limiting serial dilution, screening and selection of high expressing cell lines. Alternatively, entirely new cell lines producing the protein are generated with the intent that the new cell lines will be high expressing lines.

However, neither of these approaches offer any guarantee of success and both have significant limitations. For example, identifying high expressing cell lines by subcloning from a population of low expressing cells is limited by the relative rarity of high expressing cells in the population as well as the extensive amounts of time and labor required for the identification of any high expressing cells. Further, new cell lines producing the antibody or protein of interest may not continue to be high expressing, due to silencing of the transgene expression during expansion and growth of the cell line or other forms of genetic or epigenetic instability. (Insulators would not help)

Thus, a need exists for compositions, methods, and cells that effectively increase peptide chain expression.

SUMMARY OF THE INVENTION

Figure 1:
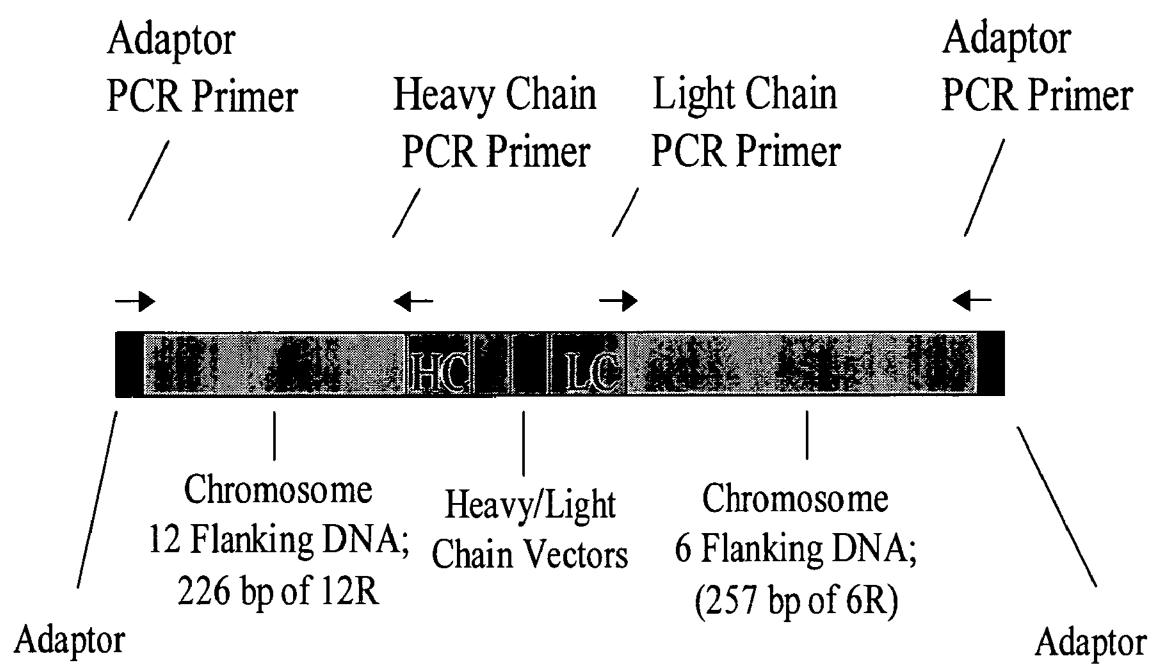
FIG. 1 shows the PCR based cloning strategy used to isolate a 257 bp and 226 bp DNA flanking the heavy chain and light chain recombination site in C128D cells.

An aspect of the invention is an isolated DNA comprising a nucleic acid having the sequence shown in SEQ ID NO: 1 and SEQ ID NO: 2.

Another aspect of the invention is an isolated DNA consisting essentially of a nucleic acid having the sequence shown in SEQ ID NO: 1, 2, 3, 4, 5, 6, 7 or 8.

Another aspect of the invention is an isolated DNA comprising a nucleic acid having the sequence shown in SEQ ID NO: 1, 2, 3, 4, 5, 6, 7 or 8 operably linked to a recombinant DNA encoding a peptide chain.

Another aspect of the invention is an isolated DNA comprising a nucleic acid having the sequence shown in SEQ ID NO: 1 and SEQ ID NO: 2 operably linked to a recombinant DNA encoding a peptide chain.

Yet another aspect of the invention is a method of producing a peptide chain expression host cell comprising the steps of providing a eukaryotic cell; introducing into the cell a DNA comprising a nucleic acid having the sequence shown in SEQ ID NO: 1, 2, 3, 4, 5, 6, 7 or 8 or both SEQ ID NO: 1 and SEQ ID NO: 2; and identifying a cell in which the introduced DNA is operably linked to a DNA encoding a peptide chain.

Another aspect of the invention is a method of producing a peptide chain expression host cell comprising the steps of providing a eukaryotic cell; and introducing into the cell a DNA comprising a nucleic acid having the sequence shown in SEQ ID NO: 1, 2, 3, 4, 5, 6, 7, or 8 or SEQ ID NO: 1 and 2 operably linked to a DNA encoding a peptide chain.

Another aspect of the invention is a method of producing a peptide chain expression host cell comprising the steps of providing a eukaryotic cell containing a nucleic acid having the sequence shown in SEQ ID NO: 1, 2, 3, 4, 5, 6, 7, or 8 or SEQ ID NO: 1 and SEQ ID NO: 2; introducing into the cell a DNA encoding a peptide chain; and identifying a cell in which the introduced DNA is operably linked to SEQ ID NO: 1, 2, 3, 4, 5, 6, 7 or 8 or SEQ ID NO: 1 and 2.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a cell" is a reference to one or more cells and includes equivalents thereof known to those skilled in the art.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, exemplary methods, devices and materials are now described.

The term "operably linked" means any linkage between nucleic acid sequences, regardless of orientation or distance, where the linkage functions to permit a first sequence or set of sequences to increase the expression of a peptide chain encoded by a second sequence, provided that the second sequence is not genomic DNA from mouse strain C57BL/6J chromosome 6 or 12. Such linkages can include physical linkages.

The term "recombinant DNA" means DNA which has been removed from its native context or which is a non-naturally occurring DNA. Recombinant DNA can be used to express recombinant peptide chains as defined below.

The term "peptide chain" means a molecule comprising at least two amino acid residues linked by peptide bonds to form a chain. Large peptide chains of more than 50 amino acids may be referred to as "polypeptides" or "proteins." Small peptide chains of less than 50 amino acids may be referred to as "peptides."

The term "antibodies" as used herein is meant in a broad sense and includes immunoglobulin or antibody molecules including polyclonal antibodies, monoclonal antibodies including murine, human, humanized and chimeric monoclonal antibodies, recombinently engineered monocolonal antibodies and antibody fragments.

In general, antibodies are proteins or polypeptides that exhibit binding specificity to a specific antigen. Intact antibodies are heterotetrameric glycoproteins, composed of two identical light chains (LC) and two identical heavy chains (HC). Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragment" means a portion of an intact antibody. This portion may be a heavy chain sequence, light chain sequence, antigen binding or variable region of an intact antibody. Examples of antibody fragments include Fab, Fab', $F(ab')_2$ and Fv fragments, diabodies, single chain antibody molecules and multispecific antibodies formed from at least two intact antibodies.

The term "expression host cell" means a cell that expresses a particular peptide chain.

The present invention relates to DNAs that increase peptide chain expression when operably linked to a gene encoding the peptide chain. The DNAs can be used singly or in combination with each other. The invention also relates to methods of generating a peptide chain expression host cell using the foregoing and the host cells generated by the method.

Figure 6:
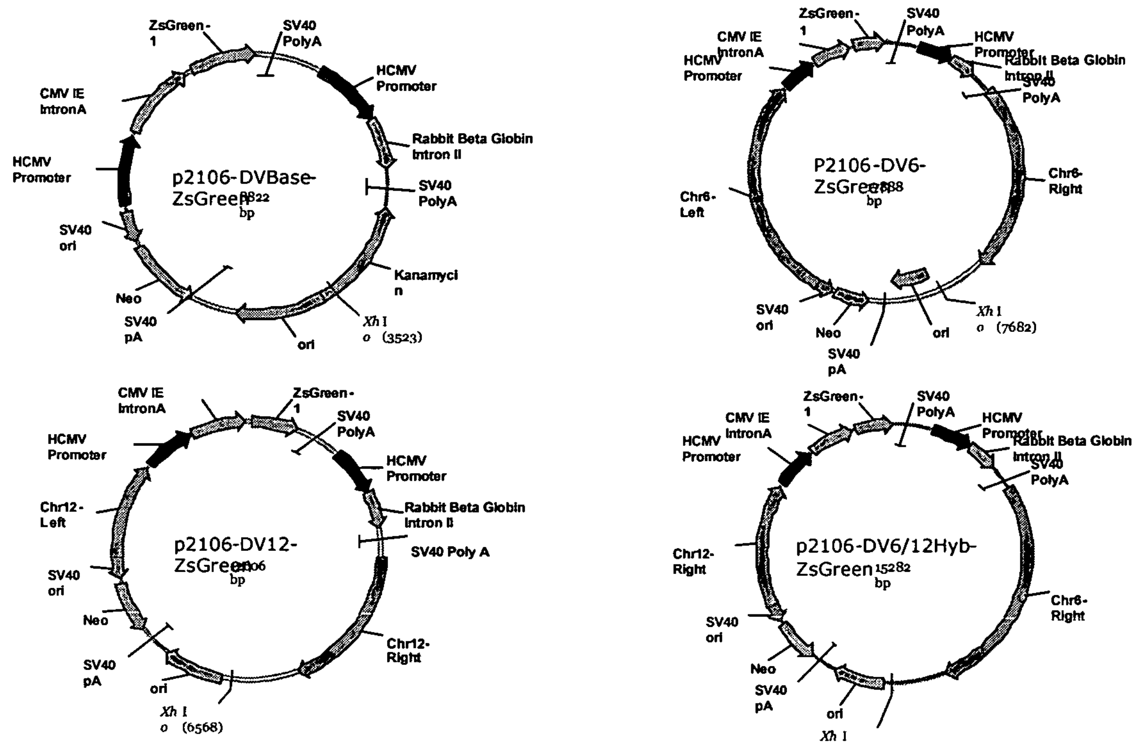
FIG. 6 shows vector maps for plasmids p2106-DVBase-ZsGreen, p2106-DV6-ZsGreen, p2106-DV12-ZsGreen, and p2106-DV6/12Hyb-ZsGreen.

One aspect of the invention is an isolated DNA comprising the nucleic acid sequence shown in SEQ ID NO: 1 and SEQ ID NO: 2, 3, 4, 5, 6, 7, or 8. Another aspect of the invention is an isolated DNA consisting of or consisting essentially of the nucleic acid sequence shown in SEQ ID NO: 1, 2, 3, 4, 5, 6, 7, or 8. These DNAs may be used to increase the expression of genes to which they are operably linked. The plasmids p2106-DV6/12Hyb-ZsGreen and pDG-GS-6R/12R, shown in FIGS. 6 and 9 respectively, are examples of such DNAs.

Another aspect of the invention is an isolated DNA comprising the nucleic acid sequence shown in SEQ ID NO: 1, 2, 3, 4, 5, 6, 7, or 8 operably linked to a recombinant DNA encoding a peptide chain. Such DNAs may be used to increase the expression of peptide chains encoded by the recombinant DNA. Examples of recombinant DNAs include genomic DNAs and artificial DNAs such as cDNAs. Genomic DNAs may be isolated from the DNA of any species or cell type. Genomic DNAs include chromosomal and organelle DNA. Artificial DNAs may contain, for example, cDNA sequences spliced to introns such as intronic enhancer elements, DNAs that are the result of rational design, or artificial DNAs comprising sequences originating from different organisms. Portions of such sequences may originate from different organisms such as, for example, *Homo sapiens* (human) or *Mus musculus* (mouse) origin. Those skilled in the art will also recognize other recombinant DNAs within the scope of the invention.

In one embodiment of the invention, the recombinant DNA operably liked to a nucleic acid having the sequence shown in SEQ ID NO: 1, 2, 3, 4, 5, 6, 7 or 8 is a cDNA. Such cDNAs may code for a peptide chain and contain no introns. However, in some instances it will be desirable to flank portions of cDNA with DNAs encoding intronic elements. Plasmid p2106-DV6-ZsGreen (shown in FIG. 6) is an example of a recombinant DNA in which a cDNA is flanked by intronic elements. cDNAs may be derived from the nucleic acids of any species. For example, a cDNA may be of human origin or mouse origin.

In another embodiment, the recombinant DNAs operably linked to a nucleic acid sequence having the sequence shown in SEQ ID NO: 1, 2, 3, 4, 5, 6, 7 or 8 may be genomic DNAs obtained from the genomes of *Mus musculus* strains such as the BALB/c or NAKED strains. These recombinant DNAs may also be genomic DNAs from other closely related members of the *Mus* genus such as *Mus domesticus* and *Mus booduga*, or the genomes of other species such as humans. Alternatively such DNAs may be recombinant DNAs including cDNAs or other artificial DNAs. Those skilled in the art will recognize other recombinant DNAs within the scope of this embodiment of the invention.

In another embodiment of the invention, a nucleic acid having the sequence shown in SEQ ID NO: 1 is operably linked on the 3' side of a recombinant DNA encoding a peptide chain. The nucleic acid may be regarded as being linked on the 3' side of the recombinant DNA if it is located on the same DNA strand and on the 3' side of the sense coding sequence of the recombinant DNA; alternatively, it may also be regarded as being linked on the 3' side of the recombinant DNA if it is located on a DNA strand complementary to a 3' portion of the strand containing the recombinant DNA. Such linkage may be direct, with no intervening sequences, or indirect with intervening sequences of any type present.

In another embodiment of the invention the isolated DNA comprising a nucleic acid having the sequence shown in SEQ ID NO: 1, 2, 3, 4, 5, 6, 7 or 8 operably linked to a recombinant DNA encoding a peptide chain further comprises an isolated DNA encoding a glutamine synthetase. Such DNAs encoding a glutamine synthetase may be derived from any organism provided they are capable of correcting a host cell glutamine metabolism deficiency. Such a metabolic deficiency can be used as the basis for the selection of cells containing the DNA of the invention. As those skilled in the art will recognize the "GS Expression System" offered by Lonza Biologics plc (Slough, UK) is one such glutamine metabolism deficiency selection and expression system. In one mode of practicing the invention, the glutamine synthestase gene is derived from this "GS Expression System."

In another embodiment of the invention the recombinant DNA operably linked to a nucleic acid having the sequence shown in SEQ ID NO: 1, 2, 3, 4, 5, 6, 7 or 8 encodes a peptide chain that is an antibody fragment. Such antibody fragments may be HC or LC fragments from an IgG isotype therapeutic antibody, or other therapeutic antibody fragments such as a Fab. Those skilled in the art will recognize other antibody fragments from other antibodies, such as diagnostic antibodies, which are also within the scope of the invention.

In another embodiment of the invention, the nucleic acid having the sequence shown in SEQ ID NO: 2, 3, 4, 5, 6, 7 or 8 is operably linked on the 5' side of a recombinant DNA encoding a peptide chain. The nucleic acid having the sequence shown in SEQ ID NO: 2 may be regarded as being linked on the 5' side of the recombinant DNA if it is located on the same DNA strand and on the 5' side of the recombinant DNA; alternatively, the nucleic acid may also be regarded as being linked on the 5' side of the recombinant DNA if it is located on a DNA strand complementary to a 5' portion of the stand containing the recombinant DNA. Such linkage may be direct, with no intervening sequences, or indirect with intervening sequences of any type present.

Another aspect of the invention is an isolated DNA comprising nucleic acids having the sequences shown in SEQ ID NO: 1 and SEQ ID NO: 2 operably linked to a recombinant DNA encoding a peptide chain. Such DNAs may be used to increase the expression of peptide chains encoded by the recombinant DNA. Recombinant DNAs and specific examples of recombinant DNAs within the scope of the invention are discussed above.

In one embodiment of the invention the recombinant DNA operably linked to nucleic acids having the sequences shown in SEQ ID NO: 1 and SEQ ID NO: 2 is a cDNA. cDNAs within the scope of the invention are described above.

In another embodiment of the invention nucleic acid having the sequence shown in SEQ ID NO: 1 is operably linked on the 3' side of the recombinant DNA and nucleic acid having the sequence shown in SEQ ID NO: 2, 3, 4, 5, 6, 7 or 8 is operably linked on the 5' side of a recombinant DNA encoding a peptide chain. Operable linkage of nucleic acid having the sequence shown in SEQ ID NO: 1 on the 3' side of the recombinant DNA is described above. Operable linkage of nucleic acid having the sequence shown in SEQ ID NO: 2, 3, 4, 5, 6, 7, or 8 on the 5' side of the recombinant DNA is also described above.

In another embodiment of the invention the isolated DNA comprising nucleic acids having the sequences shown in SEQ ID NO: 1 and SEQ ID NO: 2 operably linked to a recombinant DNA encoding a peptide chain further comprises an isolated DNA encoding a glutamine synthetase. Such DNAs encoding a glutamine synthetase are described and discussed above. As described above, in one mode of practicing the invention the glutamine synthestase gene is derived from the "GS Expression System."

In another embodiment of the invention the recombinant DNA operably linked to nucleic acids having the sequences shown in SEQ ID NO: 1 and SEQ ID NO: 2 encodes a peptide chain that is an antibody fragment. Such antibody fragments and examples thereof are described above.

Another aspect of the invention is a method of producing a peptide chain expression host cell comprising the steps of providing a eukaryotic cell; introducing into the cell a DNA comprising a nucleic acid having the sequence shown in SEQ ID NO: 1, 2, 3, 4, 5, 6, 7 or 8 or both SEQ ID NO: 1 and SEQ ID NO: 2; and identifying a cell in which the introduced DNA is operably linked to a DNA encoding a peptide chain.

A eukaryotic cell useful in the methods of the invention may be of any origin. Exemplary eukaryotic cells may be those of human and rodent origin such as *Mus musculus* (house mouse) and *Cricetulus griseus* (Chinese hamster) or the cells of other eukaryotic species such as insects. HEK-293 cells (ATCC: CRL-1573™) are an example of human derived cells. CHO-K1 (ATCC: CRL-9618™) cells are an example of Chinese hamster derived cells. Sp2/0 cells (ATCC: CRL-1851™) are an example of mouse strain BALB/c derived cells. Those skilled in the art will recognize other eukaryotic cells useful in the methods of the invention.

A eukaryotic cell provided for use in the methods of the invention may be isolated or part of a population of cells. Such populations of eukaryotic cells may be clonal (homogeneous) or heterogeneous. A eukaryotic cell that is part of a population of homogeneous or heterogeneous cells may be part of a tissue or organ.

A eukaryotic cell may be maintained in any suitable media, such as chemically defined media or serum containing media. Cells may be cultured in any suitable culture system vessel such as flasks, bioreactors, wave bags and other vessels. Those skilled in the art will recognize other media, culture system vessels, and related methods useful in the methods of the invention.

A DNA comprising a nucleic acid having the sequence shown in SEQ ID NO: 1, 2, 3, 4, 5, 6, 7 or 8 or both SEQ ID NO: 1 and SEQ ID NO: 2 may be introduced into a cell by a number of different methods such as transfection or viral infection using vectors well known to those skilled in the art such as a plasmid, transposon, DNA virus, or another fusion partner cell. These DNAs may also be introduced into a cell as a naked DNA without the use of a vector. Such DNAs may also be introduced into a cell by means of an RNA virus containing nucleic acid sequences that can be reverse transcribed inside the viral host cell to the nucleic acid having the sequence shown in SEQ ID NO: 1, 2, 3, 4, 5, 6, 7 or 8 or SEQ ID NO: 1 and 2. Methods of transfection include, for example, lipofection and electroporation. Methods of viral infection include, for example, the use of a helper virus to permit infection by a second virus. Virus based DNA introduction methods may be used to introduce a DNA into an isolated cell or a homogenous or heterogeneous population of cells. Those skilled in the art will recognize many other methods and vectors for introducing a DNA into a cell.

Markers linked to a nucleic acid having the sequence shown in SEQ ID NO: 1, 2, 3, 4, 5, 6, 7 or 8 or SEQ ID NO: 1 and 2 or co-introduced into cells with these DNAs can be used to screen for cells into which these DNAs have been introduced. Such markers can be any nucleic acid sequence that can be used to identify cells into which the particular marker sequence has been introduced. The marker may be, for example, a gene that can be used to identify cells having a phenotype associated with the particular gene. Such markers may be used for screening or selection of cells on the basis of the marker-associated phenotype. Drug resistance genes are one class of markers that are well known in the art. Rescue genes that permit cells with metabolic, temperature sensitivity, or other deficiencies to survive are an example of another class of markers. Markers may also be genes that control expression of a particular phenotype at the transcriptional level; inducible promoters are an example of this class of marker. Genes expressing a readily detectable polypeptide, or other biomolecule such as a lectin, are another class of markers. Genes encoding antibodies or proteins capable of emitting light, such as luciferases or fluorescent proteins are examples of markers in this class. A marker may also be a nucleic acid sequence that can be used, even in the absence of a specific phenotype associated with the nucleic acid sequence, to identify cells into which the particular sequence has been introduced. As those skilled in the art will recognize, PCR with primers specific to such marker sequences can be used to identify cells into which markers of this type have been introduced. Those skilled in the art will recognize that cell sorting based techniques, such as fluorescence activated cell sorting (FACS), may be used to facilitate the identification of cells harboring a marker. Those skilled in the art will also recognize other markers and related techniques.

Identification of a cell in which an introduced DNA having the sequence shown in SEQ ID NO: 1, 2, 3, 4, 5, 6, 7 or 8 or both SEQ ID NO: 1 and SEQ ID NO: 2 are operably linked to a DNA encoding a peptide chain can be readily accomplished. This can be done by comparing expression of a peptide chain by a control cell with the peptide chain expression level in a cell after the introduction of a DNA comprising a nucleic acid having the sequence shown in SEQ ID NO: 1, 2, 3, 4, 5, 6, 7 or 8 or SEQ ID NO: 1 and SEQ ID NO: 2 into the cell. A DNA comprising a nucleic acid having the sequence shown in SEQ ID NO: 1, 2, 3, 4, 5, 6, 7, or 8 or SEQ ID NO: 1 and SEQ ID NO: 2 is operably linked to the DNA encoding the peptide chain when peptide chain expression in cells receiving such DNA is increased relative to the control cell. This phenotype is diagnostic of operable linkage.

A DNA comprising a nucleic acid having the sequence shown in SEQ ID NO: 1, 2, 3, 4, 5, 6, 7 or 8 or SEQ ID NO: 1 and SEQ ID NO: 2 may become operably linked to the DNA encoding the peptide chain in at least two different ways. Operable linkage can be effected prior to introduction into a cell by physically linking a DNA comprising a nucleic acid having the sequence shown in SEQ ID NO: 1, 2, 3, 4, 5, 6, 7 or 8 or SEQ ID NO: 1 and SEQ ID NO: 2 to the DNA encoding the peptide chain in a conformation known to, or reasonably likely to, produce an operable linkage. Alternatively, operable linkage can be effected after introduction of a DNA comprising a nucleic acid having the sequence shown in SEQ ID NO: 1, 2, 3, 4, 5, 6, 7 or 8 or SEQ ID NO: 1 and SEQ ID NO: 2 into a cell. This can be accomplished via in vivo recombination events that produce an operable linkage between these DNAs.

Such recombination events can be targeted to occur at a specific DNA sequence or can be permitted to occur at a random DNA sequence. Recombination events can involve genomic DNA, such as chromosomal or organelle DNA, or non-genomic DNA such as extra-chromosomally maintained plasmid DNAs or artificial chromosomes. Recombination events can be targeted to occur at a specific DNA sequence by using a linearized DNA that contains several kilo-bases of sequence identical to the target DNA in addition to a DNA comprising a nucleic acid having the sequence shown in SEQ ID NO: 1, 2, 3, 4, 5, 6, 7 or 8 or SEQ ID NO: 1 and SEQ ID NO: 2. Strategies and related methods for targeting recombination events to a specific DNA sequence in order to introduce a heterologous DNA sequence are well known in the art (See, e.g., Harris et al., *Exp. Cell Res.* 253, 523-532 (1999)) and are routinely employed in the generation of transgenic animals, cells and cell lines. Random recombination events can occur by introducing linear DNAs lacking target DNA sequence or simply introducing non-linearized, circular plasmid DNAs into a cell. Those skilled in the art will recognize other methods and strategies to achieve in vivo recombination events that produce an operable linkage between DNAs.

Another aspect of the invention is a method of producing a peptide chain expression host cell comprising the steps of providing a eukaryotic cell; and introducing into the cell a DNA comprising a nucleic acid having the sequence shown in SEQ ID NO: 1, 2, 3, 4, 5, 6, 7 or 8 or both SEQ ID NO: 1 and SEQ ID NO: 2 operably linked to a DNA encoding a peptide chain. The eukaryotic cell may be as described above. In this aspect of the invention, operable linkage is effected prior to introduction into a cell by physically linking a DNA comprising a nucleic acid having the sequence shown in SEQ ID NO: 1, 2, 3, 4, 5, 6, 7 or 8 or SEQ ID NO: 1 and SEQ ID NO: 2 to the DNA encoding the peptide chain in a conformation known to, or reasonably likely to, produce an operable linkage.

Another aspect of the invention is a method of producing a peptide chain expression host cell comprising the steps of providing a eukaryotic cell comprising a nucleic acid having the sequence shown in SEQ ID NO: 1, 2, 3, 4, 5, 6, 7 or 8 or SEQ ID NO: 1 and SEQ ID NO: 2; introducing into the cell a DNA encoding a peptide chain; and identifying a cell in which the introduced DNA is operably linked to the nucleic acid having the sequence shown in SEQ ID NO: 1, 2, 3, 4, 5, 6, 7 or 8 or SEQ ID NO: 1 and SEQ ID NO: 2. Cells containing a nucleic acid having the sequence shown in SEQ ID NO: 1, 2, 3, 4, 5, 6, 7 or 8 or SEQ ID NO: 1 and 2 can be readily identified by PCR based techniques, fluorescent in situ hybridization (FISH), or other hybridization based techniques well known in the art such as Southern blotting. Molecular cloning techniques in conjunction with nucleic acid sequencing can also be used to identify cells containing these sequences.

In this aspect of the invention the DNA encoding a peptide chain may be introduced into the cell by any of the methods discussed above or other methods well known in the art. Such introduced DNA can become operably linked to a nucleic acid having the sequence shown in SEQ ID NO: 1, 2, 3, 4, 5, 6, 7 or 8 or SEQ ID NO: 1 and SEQ ID NO: 2 via in vivo recombination events that produce an operable linkage between these DNAs. Such recombination events can be targeted to occur at a specific DNA sequence or can be permitted to occur at a random DNA sequence.

Another embodiment of the invention is a cell produced by the methods of the invention. Yet another embodiment of the invention is a method of producing a peptide chain comprising culturing the cell produced by the methods of the invention.

The present invention will now be described with reference to the following specific, non-limiting examples.

EXAMPLE 1

Isolation of Chromosomal DNA Sequences Flanking Two Recombinant Genes Highly Expressed in C128D Cells The C128D cell line is a Sp2/0 *Mus musculus* strain BALB/c myeloma derived cell line that has been stably transfected with two recombinant DNA constructs to permit expression of a whole human/murine chimeric antibody. The first construct encoded a murine anti-CD4 HC variable region with a human G1 constant region. The second construct encoded a murine anti-CD4 LC variable region with a human kappa constant region. In C128D cells the heavy and light chain polypeptides were expressed at extremely high levels (158 mg/L in a spent shake flask; 1 g/L/day in a perfusion bioreactor). Additionally, at least one copy of the LC gene and at least one copy of the HC gene construct have integrated immediately adjacent to each other in the genomic DNA of the C128D cell line. See FIG. 1.

Figure 2:
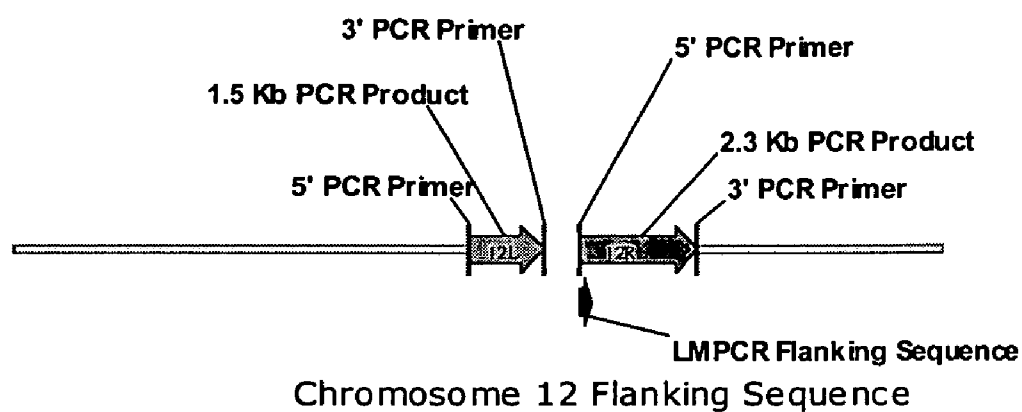
FIG. 2 shows the PCR based cloning strategy used to isolate the polynucleotides 6R (SEQ ID NO: 1), 6L, 12R (SEQ ID NO: 2), and 12L from C128D cells.
Figure 2:
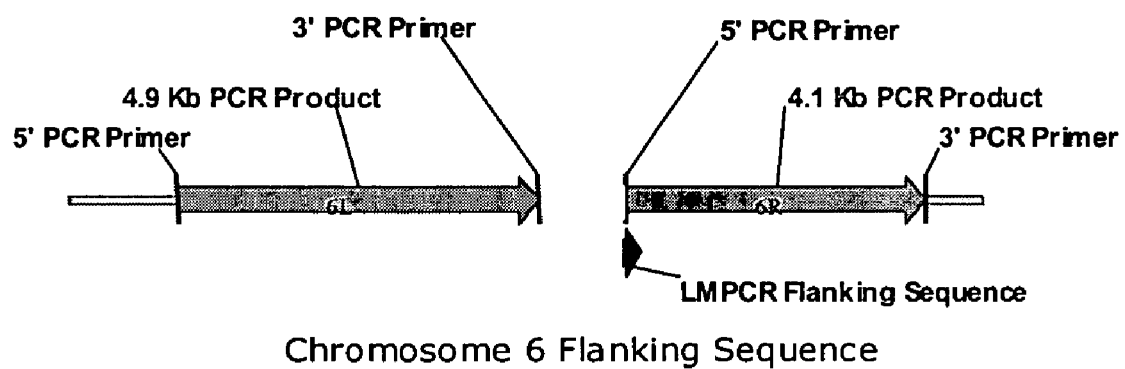

Genomic regions that flank the recombinant HC and LC genes in the C128D cell line were cloned by standard ligation mediated PCR techniques. A 257 bp, murine genomic sequence flanking the 3' side of the LC gene integration site was cloned. A 226 bp, murine genomic sequence flanking the 5' side of the HC gene integration site was also cloned. See FIGS. 1 and 2.

BLASTN analysis revealed the 257 bp fragment matched a portion of chromosome 6 of the *Mus musculus* strain C57BL/6J genome having Accession no. CAAA01122220.1. BLASTN analysis also revealed that the 226 bp fragment matched a portion of chromosome 12 of the *Mus musculus* strain C57BL/6J having Accession no. CAAA01060907. All BLASTN analyses were performed using the default settings with filtering turned off. Fluorescent in situ hybridization (FISH) analysis indicated that a chromosomal translocation had resulted in a piece of murine chromosome 6 and murine chromosome 12 being adjacent to each other at the site of HC and LC integration in the high expressing C128D cell line.

Standard PCR techniques were then used to separately clone 4152 bp of chromosome 6 DNA (6R; SEQ ID NO: 1)flanking the recombinant gene integration site and approximately 4900 bp of DNA (6L) that would have been adjacent to the integration site in the absence of the translocation. Accession no. CAAA01122220.1 was used, in part, to design primers for the PCR cloning of both 6R and 6L.

The cloned 6R sequence (SEQ ID NO: 1) had 99% identity to a 4152 bp portion of Accession no. CAAA01122220.1. Accession no. CAAA01122220.1 is a *Mus musculus* C57BL/6J strain whole genome shotgun assembly contig containing 12538 bp of chromosome 6. Those portions of Accession no. CAAA01122220.1 corresponding to the cloned 6R and 6L fragments have not been reported to contain DNA sequences capable of increasing gene expression.

Standard PCR techniques were also used to clone 2304 bp of chromosome 12 DNA (12R; SEQ ID NO: 1)flanking the recombinant gene integration site and approximately 1500 bp of DNA (12L) that would have been adjacent to the recombinant gene integration site in the absence of the translocation. Accession no. CAAA01060907 was used, in part, to design primers for the PCR cloning of both 12R and 12L.

The cloned 12R sequence (SEQ ID NO: 2) had 99% identity to a 4152 bp portion of Accession no. CAAA01060907. Accession no. CAAA01060907 is a *Mus musculus* C57BL/6J strain whole genome shotgun assembly contig containing 18296 bp of chromosome 6. Those portions of Accession no. CAAA01122220.1 corresponding to the cloned 6R and 6L fragments have not been reported to contain DNA sequences capable of increasing gene expression.

The PCR cloning of 6L and 12L as well as FISH data indicated that C128D cells do not contain the 6L and 12L DNA at the site of recombinant gene integration, but these elements were present elsewhere in the DNA of C128D cells. Importantly, data generated by FISH and PCR analyses indicated that the order of DNA elements at the site of recombinant gene integration in C128D cells was 5'-12R-HC-LC-6R-3' (shown in FIG. 1). These data indicate that the 6L and 12L DNAs do not contribute to increased recombinant gene expression in C128D cells.

EXAMPLE 2

The 6R and 12R DNAs Increase Recombinant Reporter Gene Expression in Stably Transfected Eukaryotic Cells Vector constructs containing the 6R, 6L, 12R, and 12L DNAs linked to a Green Fluorescent Protein (GFP) reporter gene were made to facilitate the identification of elements that increase recombinant gene expression. All vectors were constructed using standard molecular biology techniques and the plasmid maps are all shown in FIG. 6.

The p2106-DVBase-ZsGreen (DV-BASE) vector contains a cDNA encoding a ZsGreen GFP reporter gene derived from a *Zoanthus* sp. Coral (Matz et al., *Nature Biotechnology,* 17, 969-973 (1999). The reporter gene in DV-BASE is not linked to the 6R, 6L, 12R, or 12L DNAs. In the p2106-DV6-ZsGreen (DV-6) vector the 6L DNA is linked on the 5' side of the GFP reporter gene and the 6R DNA is linked on the 3' side of the GFP gene. In the p2106-DV12-ZsGreen (DV-12) vector the 12R DNA is linked on the 3' side of the GFP reporter gene and the 12L DNA is linked on the 5' side of the GFP gene. In the p2106-DV6/12Hyb-ZsGreen (DV-6/12) vector the 12R DNA is linked on the 5' side of the GFP reporter gene and the 6R DNA is linked on the 3' side of the GFP gene. DV-6/12 represents the 5'-12R-RECOMBINANT GENE-6R-3'type arrangement of the 6R and 12R DNA elements found in C128D cells. C128D cells do not contain the 6L and 12L DNAs at the site of recombinant gene integration. The DV-6, DV-12, and DV-6/12 vectors are otherwise identical to the DV-BASE vector.

CHOK1-SV or HEK-293 cells were stably transfected with the DV-BASE, DV-6, DV-12, or DV-6/12 vectors. GFP expression was then assessed to determine whether the 6R, 6L, 12R, and 12L flanking DNAs increased GFP expression. CHOK1-SV cells are derived from Chinese Hamster ovary cells. HEK-293 cells are derived from human kidney cells. Stable transfectants were selected for growth in media containing 400 μg/ml G418 in bulk culture and subcloned by limiting dilution into 96 well plates. HEK-293 cells were cultured in Freestyle 293 Expression Media (Cat. No. 12338-018, Invitrogen, Corp. Carlsbad, Calif.). CHOK1-SV cells were cultured in DMEM+10% FBS+6 mM Glutamine at 37° C. in an atmosphere of 5% $CO_2$ using standard cell culture techniques.

Figure 3:
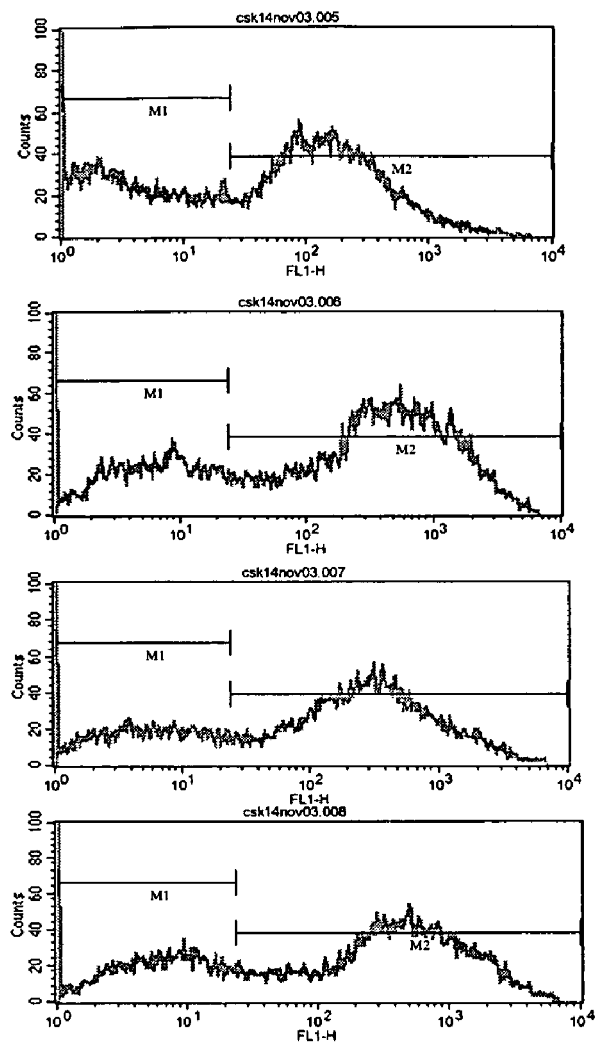
FIG. 3 shows flow cytometry analysis of Green Fluorescent Protein expression by a population of CHOK1-SV cells stably transfected with plasmids p2106-DVBase-ZsGreen, p2106-DV6-ZsGreen, p2106-DV12-ZsGreen, or p2106-DV6/12Hyb-ZsGreen.
Figure 4:
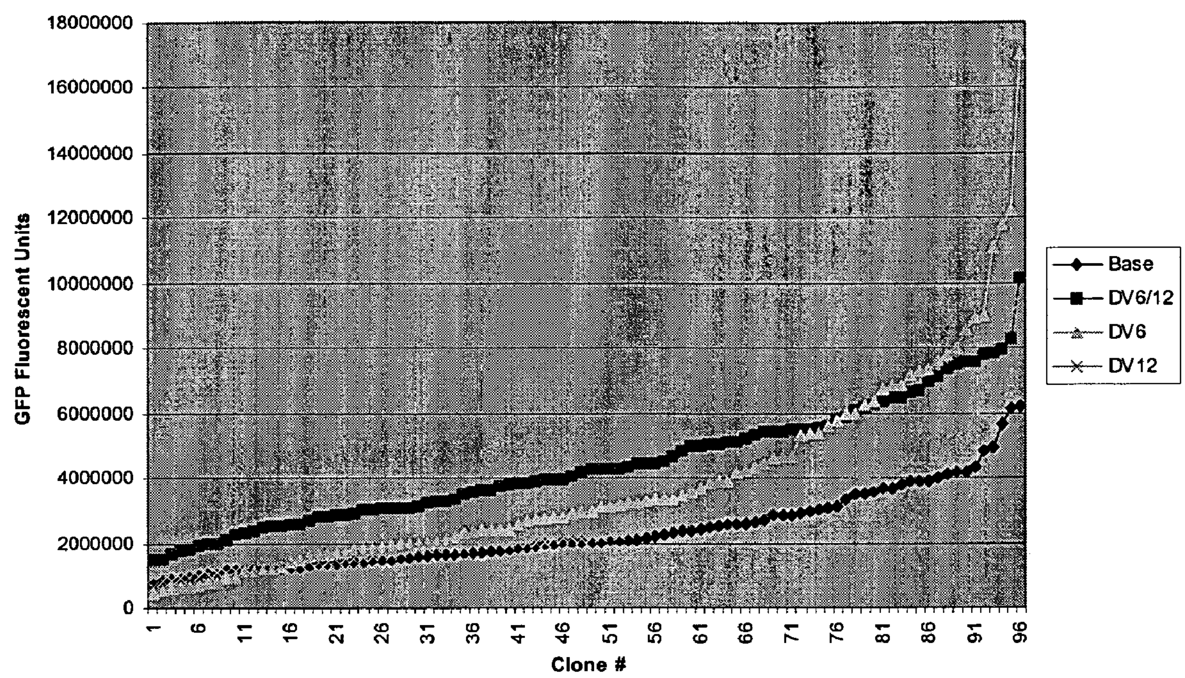
FIG. 4 shows fluorescent imaging analysis of Green Fluorescent Protein expression by individual CHOK1-SV cells stably transfected with plasmids p2106-DVBase-ZsGreen, p2106-DV6-ZsGreen, p2106-DV12-ZsGreen, or p2106-DV6/12Hyb-ZsGreen.

The data shown in FIGS. 3 and 4 indicates that GFP expression is increased, relative to controls, in CHOK1-SV cells stably transfected with vectors in which the 6R and 12R DNAs are linked to the GFP reporter gene. Flow cytometry analysis using standard methods and instrumentation was performed on bulk populations of CHOK1-SV cells stably transfected with DV-BASE, DV-6, DV-12, or DV-6/12 to assess GFP expression. This flow cytometry analysis demonstrated that, relative to DV-BASE transfected cells, median GFP expression was increased approximately two to three fold in DV-6, DV-12, or DV-6/12 transfected CHOK1-SV cells by linking the 6R and 12R DNAs to the GFP reporter gene.

Individual stably transfected CHOK1-SV derived cells were then isolated using standard methods and the resulting clonal populations were cultured in 96-well plates. Fluorescent imaging analysis was performed on each independently derived clonal population of stably transfected cells and populations were ranked in order of GFP expression (FIG. 4). This analysis indicated, again, that GFP expression was increased approximately two to three fold in DV-6, DV-12, or DV-6/12 transfected CHOK1-SV cells by linking the 6R and 12R DNAs to the GFP reporter gene. Fluorescent imaging analysis was performed using standard methods and instrumentation.

Figure 5:
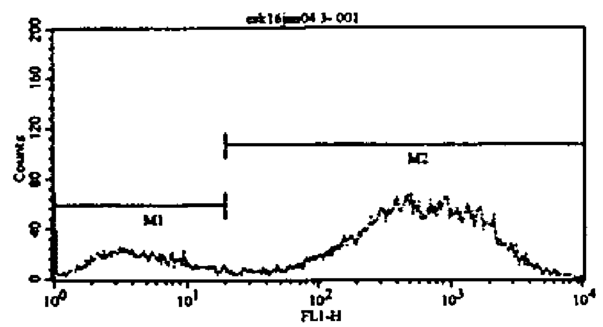
FIG. 5 shows flow cytometry analysis of therapeutic antibody expression by a population of HEK-293 cells stably transfected with plasmids p2106-DVBase-Antibody, p2106-DV6-Antibody, p2106-DV12-Antibody, or p2106-DV6/12Hyb-Antibody.
Figure 5:
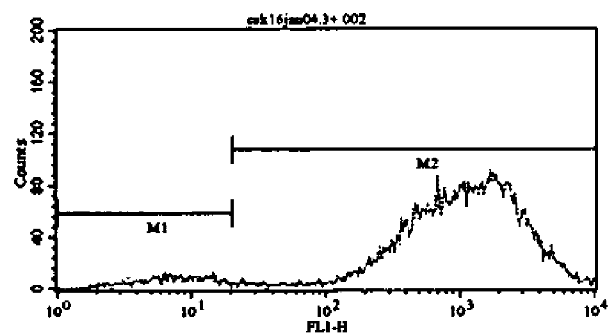
Figure 5:
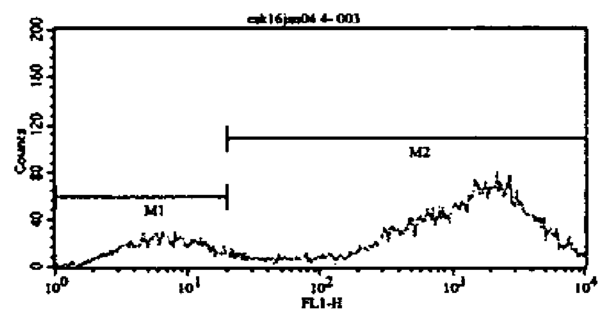
Figure 5:
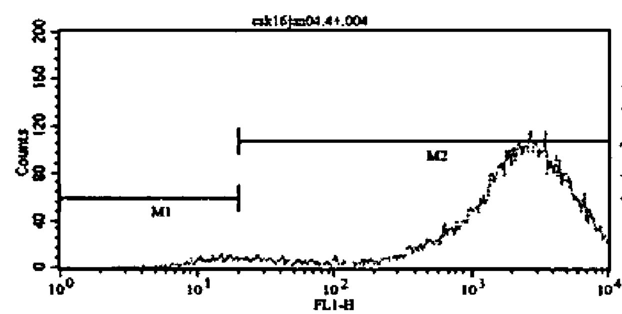

The data in FIG. 5 shows that GFP expression is also increased, relative to controls, in HEK-293 cells stably transfected with vectors in which the 6R and 12R DNAs are linked to the GFP reporter gene. Flow cytometry analysis demonstrated that, relative to DV-BASE transfected cells, median GFP expression was increased approximately two to four fold in DV-6, DV-12, or DV-6/12 transfected HEK-293 cells by linking the 6R and 12R DNAs to the GFP reporter gene. Flow cytometry analysis on bulk populations of cells was performed as described above.

Together these results indicate that the 6R and 12R DNAs can increase recombinant gene expression in eukaryotic cells derived from different species and tissues.

EXAMPLE 3

The 6R and 12R DNAs Increase Recombinant Antibody Gene Expression in Stably Transfected Human Cells Vector constructs containing the 6R and 12R DNAs linked to HC and LC genes encoding a human IgG1K antibody against IL-6 were made. One construct was the p2106-DV-Base-Antibody (DV-BASE-Ab). DV-BASE-Ab is essentially identical to p2106-DVBASE-ZsGreen (shown in FIG. 6) except that the GFP reporter gene has been replaced with the antibody HC gene and an LC gene was inserted 5' to the rabbit beta-globin intron II element present in the vector. The second construct was p2106-DV6/12Hyb-Antibody (DV6/12-Ab). DV6/12-Ab is essentially identical to p2106-DV6/12Hyb-ZsGreen (shown in FIG. 6) except that the GFP reporter gene has been replaced with the HC gene and an LC gene was inserted 5' to the rabbit beta globin intron II element present in the vector. In DV-6/12-Ab the 12R DNA is linked on the 5' side of the HC gene and the 6R DNA is linked on the 3' side of the LC gene. DV-6/12 represents the arrangement of the 6R and 12R DNA elements found in C128D cells. All vectors were constructed using standard molecular biology techniques.

HEK-293 cells were stably transfected with the DV-BASE-Ab and DV-6/12-Ab. Antibody expression in the bulk populations of stable transfectants and resulting clonal populations was assessed to determine whether the 6R and 12R flanking DNAs increased recombinant antibody gene expression. Stable transfectants were selected, cultured and subcloned as described in Example 2 above. Antibody titer in the culture media was determined using standard methods. Specific productivity, a measure of the rate of antibody secretion on a per cell basis, was also determined using standard methods.

Figure 7:
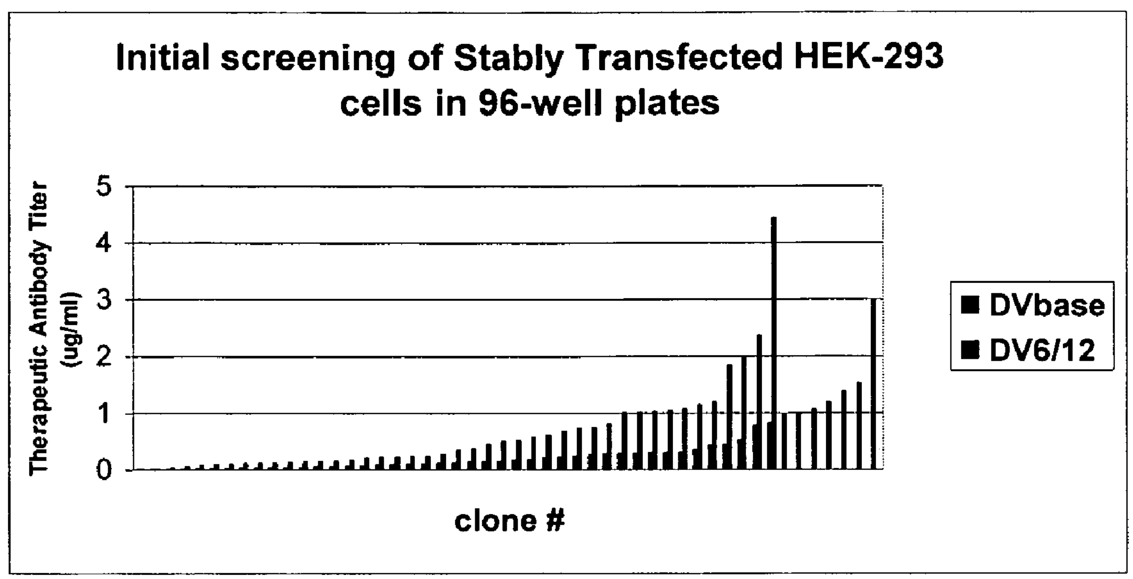
FIG. 7 shows antibody titer analysis of therapeutic antibody expression by individual HEK-293 cells stably transfected with plasmids p2106-DVBase-Antibody or p2106-DV6-Antibody.

Recombinant antibody gene expression is increased, relative to control, in HEK-293 cells stably transfected with DV-6/12-Ab (FIG. 7 and Table 1). In bulk cell populations of DV-6/12-Ab transfected cells the antibody concentration after 22 days in culture, was increased several fold relative to DV-BASE-Ab transfected cells (FIG. 7). The rate of antibody expression was also increased approximately 2.6 fold in bulk populations of DV-6/12-Ab transfected cells relative to DV-BASE-Ab transfected cells (Table 1).

TABLE 1

Titer and specific productivity analyses of therapeutic antibody expression by a population of HEK-293 cells stably transfected with p2106-DVBase-Antibody or p2106-DV6/12Hyb-Antibody.

| Expression Plasmid | Therapeutic Antibody Titer (μg/ml) | Therapeutic Antibody Specific Productivity (pg/cell/day) |
|---|---|---|
| P2106-DVBase-Antibody | 17 | 1.1 |
| p2106-DV6/12Hyb-Antibody | 47 | 2.9 |
| | Fold Increase: 2.8 | Fold Increase: 2.6 |

Individual DV-6/12-Ab and DV-BASE-Ab stably transfected HEK-293 derived cells were then isolated using standard methods and the resulting clonal populations were cultured in 96-well plates. Antibody titers in each well were determined for each independently derived clonal population of stably transfected cells and populations were ranked in order of Ab expression (FIG. 7). This analysis indicated, again, that Ab expression was increased several fold in DV-6/12-Ab transfected HEK-293 cells by linking the 6R and 12R DNAs to the GFP reporter gene (FIG. 7).

Together with the data in the examples above, these results indicate that the 6R and 12R DNAs can increase the expression of recombinant genes encoding disparate types of proteins. Furthermore, these results indicate that the ability of the 6R and 12R DNAs to increase recombinant gene expression does not appear to be limited to a specific reporter, antibody, or other recombinant gene.

EXAMPLE 4

Figure 9:
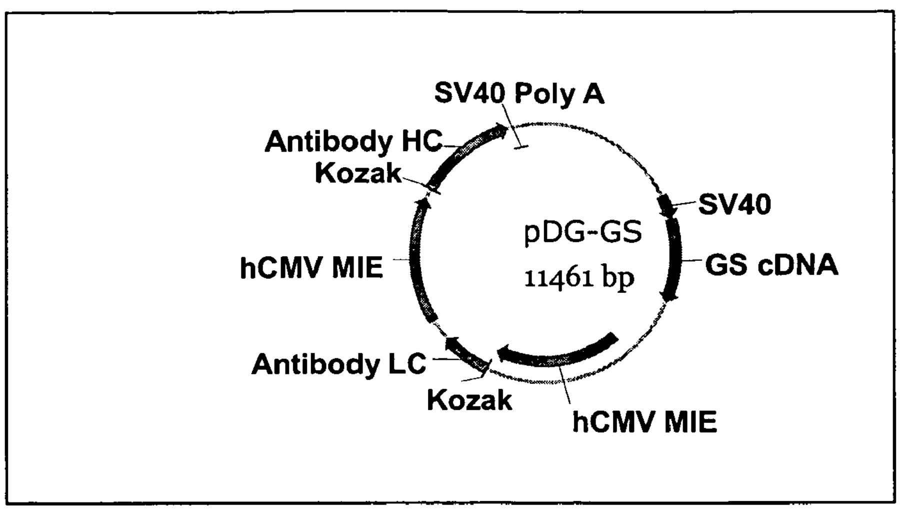
FIG. 9 shows vector maps for plasmids pDG-GS, pDG-GS-12R, and pDG-GS-6R/12R.
Figure 9:
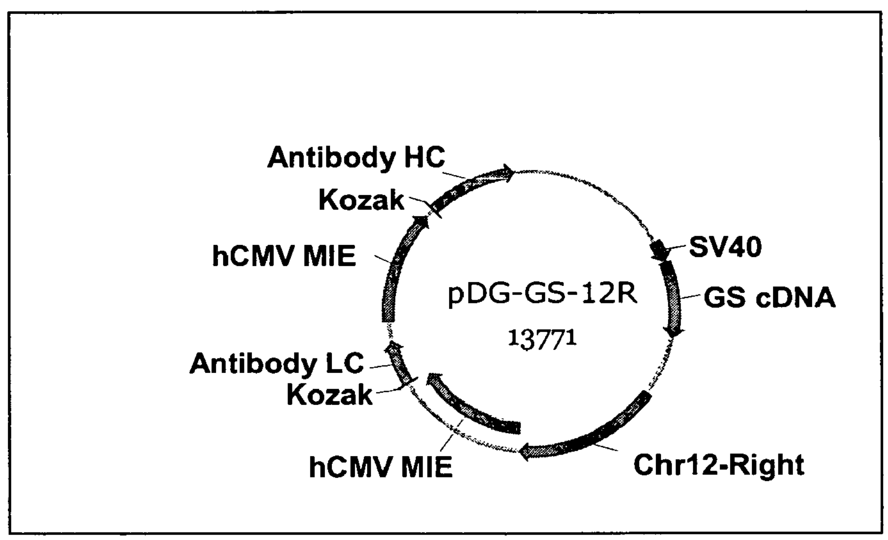
Figure 9:
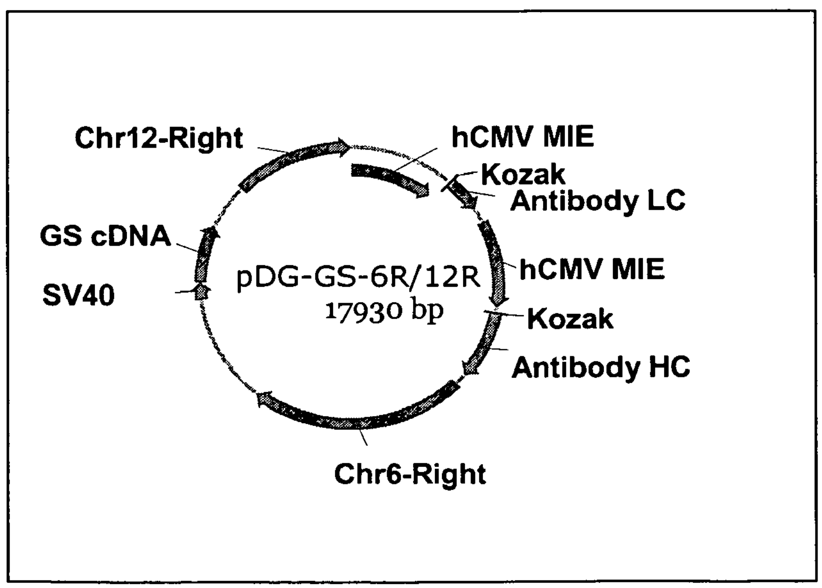

12R DNA Can Increase Recombinant Antibody Gene Expression in Stably Transfected Eukaryotic Cells Vector constructs containing the 6R and 12R DNAs linked to heavy and light chain genes encoding a human antibody against tissue factor were made as indicated (plasmid maps shown in FIG. 9). All vectors were constructed using standard molecular biology techniques.

In the pDG-GS construct, a gene encoding a therapeutic antibody LC was located 5' to the gene encoding the HC of the same antibody. A second construct, pDG-GS-12R, is essentially identical to PDG-GS except that the 12R DNA is located on the 5' side of the LC gene (FIG. 9). A third construct, pDG-GS-6R/12R, is identical to pDG-GS-12R except that the 6R DNA is located on the 3' side of the HC gene (FIG. 9). All vectors contain a glutamine synthetase (GS) selection marker.

CHOK1-SV cells were transfected with each construct and stable transfectants were selected for growth in DMEM+10% FBS+6 mM Glutamine containing 50 μM methionine sulfoximine (MSX) and for antibody production. Stable transfectants were subcloned as described in Example 2 above. Antibody titer in the culture media was determined using standard methods.

Individual pDG-GS, pDG-GS-12R, or pDG-GS-6R/12R stably transfected CHOK1-SV derived cells were isolated using standard methods and the resulting clonal populations were cultured in 24 well plates. Antibody titers in each well were determined for each independently derived clonal population of stably transfected cells and 15 clonal populations producing the highest Ab levels were ranked in order of antibody expression.

Figure 8:
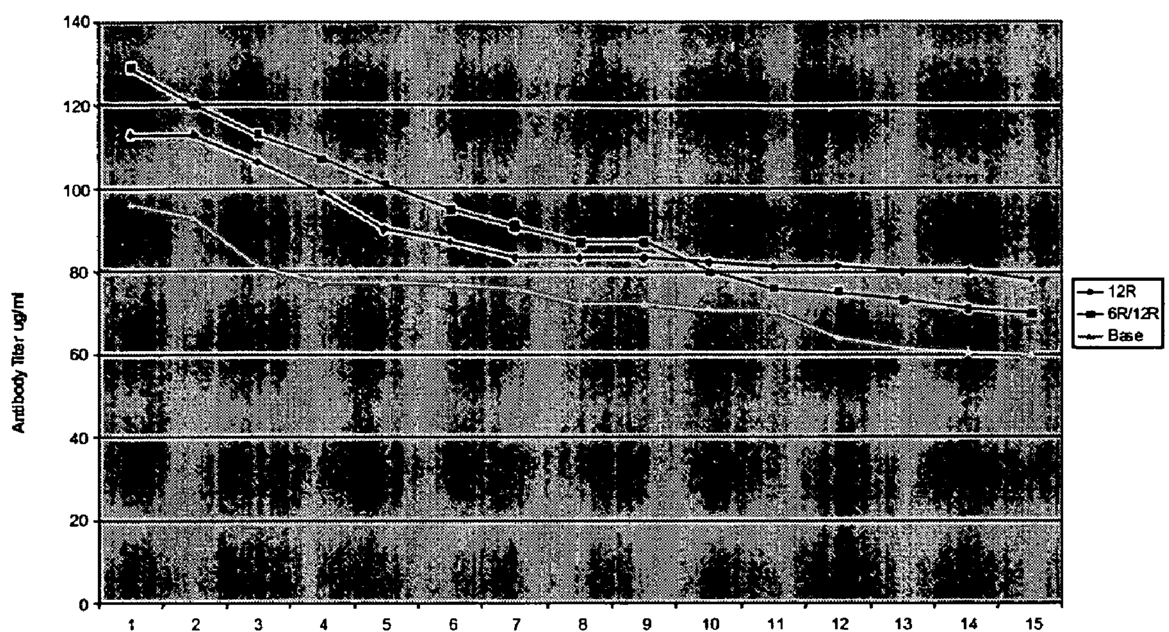
FIG. 8 shows antibody titer analysis of individual HEK-293 cells stably transfected with plasmids PDG-GS, pDG-GS-12R, or pDG-GS-6R/12R.

The data shown in FIG. 8 demonstrates that recombinant antibody gene expression and secretion rates in pDG-GS-12R and pDG-GS-6R/12R transfected cells were increased relative to control pDG-GS transfected cells. This analysis demonstrates that the 12R DNA alone can increase antibody expression relative to control.

EXAMPLE 5

Figure 11:
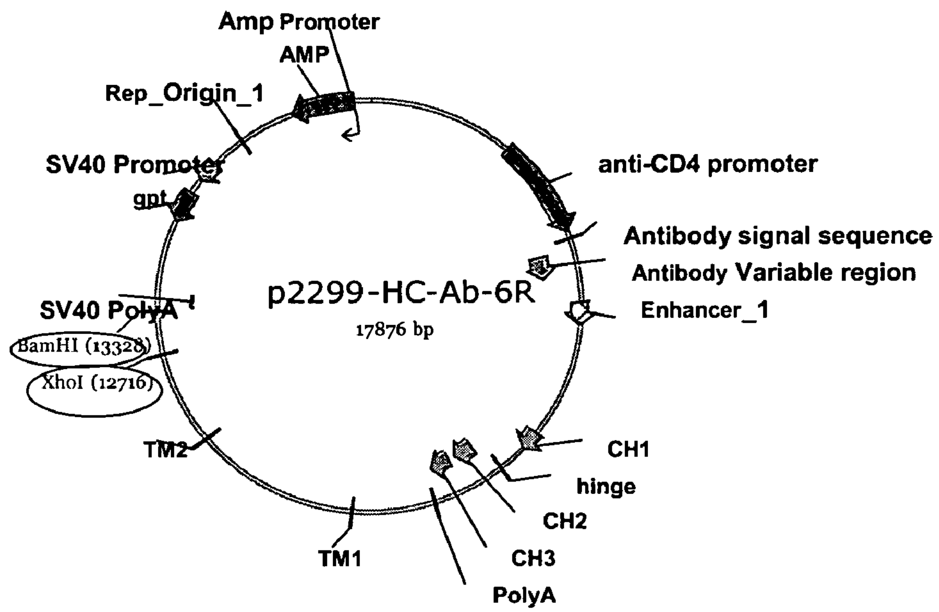
FIG. 11 shows vector maps for plasmids p2299-HC-Ab-6R and p2299-LC-Ab-6R.
Figure 11:
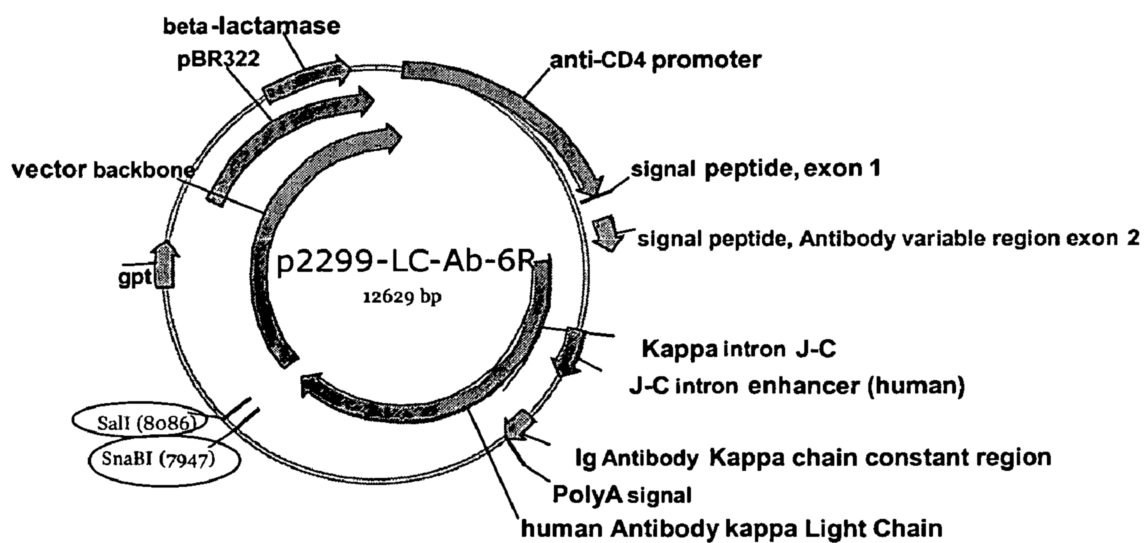

6R DNA Can Increase Recombinant Antibody Gene Expression in Stably Transfected Eukaryotic Cells Vector constructs containing 6R DNA linked to HC and LC genes encoding a murine variable/human constant chimeric antibody against IL-6 were made as indicated (plasmid map shown in FIG. 11). All vectors were constructed using standard molecular biology techniques.

The p2299-HC-Ab construct contains a cDNA encoding the HC. A second construct, p2299-LC-Ab, contains a cDNA encoding the LC. A third construct, p2299-HC-Ab-6R, is essentially identical to p2299-HC-Ab except that a single 6R DNA element is located on the 3' side of the HC gene (FIG. 11). A fourth construct, p2299-LC-Ab-6R, is essentially identical to p2299-LC-Ab except that a single 6R DNA element is located on the 3' side of the LC gene (FIG. 11). Additional 6R elements are provided in trans during transfection. All vectors contain a guanine-hypoxanthine phosphoribosyltransferase (GPT) selection marker.

C884C cells were co-transfected with either p2299-HC-Ab and p2299-LC-Ab or p2299-HC-Ab-6R, p2299-LC-Ab-6R, and a linear 6R DNA unlinked to any other DNAs. C884C cells are an NS/0 derived cell line adapted for growth in chemically defined media. The NS/0 cell line is a *Mus musculus* (mouse) myeloma cell line. Stable transfectants were selected for growth in CD-Hybridoma protein free chemically defined media (Cat. No. 11279-023, Invitrogen Corp.) containing 1X MHX (10 μg of mycophenolic acid, 15 μg of hypoxanthine, and 25 μg of xanthine per ml), 8 mM L-glutamine and 1 g/L Sodium Bicarbonate or GPT selection media and for antibody production. Stable transfectants were subcloned as described in Example 2 above. Antibody titer in the culture media was determined using standard methods.

Individual p2299-HC-Ab/p2299-LC-Ab or p2299-HC-Ab-6R/p2299-LC-Ab-6R/6R stably cotransfected cells were isolated using standard methods and the resulting primary clonal populations were cultured in 24 well plates. Secondary clones where then isolated from the primary clones after further GPT selection and cultured in 24 well plates. Antibody titers in each well containing independently derived populations of primary (data shown in Table 2) or secondary clones (data shown in Table 3) were determined and titers from clones producing the highest Ab levels were tabulated.

TABLE 2

Titer analysis of antibody expression by primary clonal populations of C884C cells stably co-transfected with p2299-HC-Ab and p2299-LC-Ab (control) or p2299-HC-Ab-6R, p2299-LC-Ab-6R, and a linear 6R DNA unlinked to any other DNAs (6R—6R).

| | Antibody Titer (μg/ml) | |
|---|---|---|
| Cotransfected DNAs | 24 Well Plate Suspension Culture | Shake Flask Suspension |
| Control | 64 | 55 |
| 6R—6R | 151 | 168 |
| | Fold increase: 2.4 | Fold increase: 3.1 |

TABLE 3

Titer analysis of antibody expression by secondary clonal populations of C884C cells stably co-transfected with p2299-HC-Ab and p2299-LC-Ab (control) or p2299-HC-Ab-6R, p2299-LC-Ab-6R, and a linear 6R DNA unlinked to any other DNAs (6R—6R).

| | Antibody Titer (μg/ml) | |
|---|---|---|
| Cotransfected DNAs | 24 Well Plate Culture in Chemically Defined Media | 24 Well Plate Culture in Chemically Defined Media Supplemented with Soy Extract |
| Control | 151 | 271 |
| 6R—6R | 282 | 457 |
| | Fold increase: 1.87 | Fold increase: 1.69 |

The data shown in Tables 2 and 3 indicates that recombinant antibody gene expression in p2299-HC-Ab-6R/p2299-LC-Ab-6R/6R stably cotransfected cells was increased approximately two to three fold relative to control p2299-HC-Ab/p2299-LC-Ab transfected cells. These results demonstrate that linking 6R DNA alone to a recombinant gene encoding an antibody can increase the antibody expression and secretion rates relative to control without any contribution from 12R DNA.

EXAMPLE 6

Nuclear Matrix Binding Activity of the 12R DNA and Its Fragments

Figure 10:
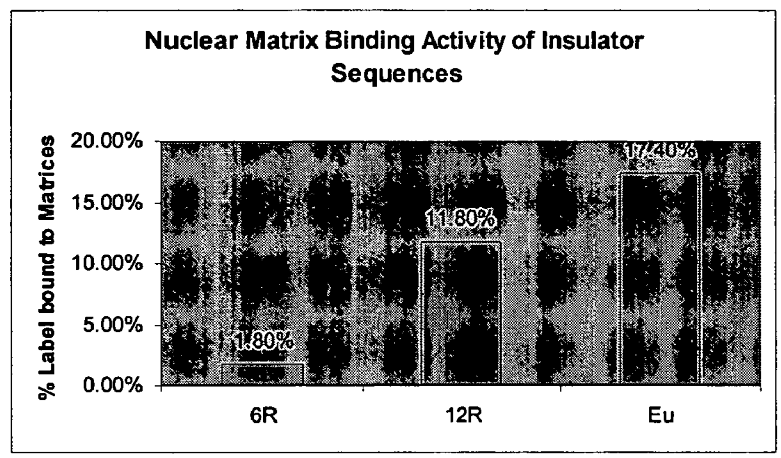
FIG. 10 shows nuclear matrix binding activity of the 12R DNA and its fragments designated A (SEQ ID NO: 3), B (SEQ ID NO: 4), C (SEQ ID NO: 5), D (SEQ ID NO: 6), E (SEQ ID NO: 7) and F (SEQ ID NO: 8).
Figure 10:
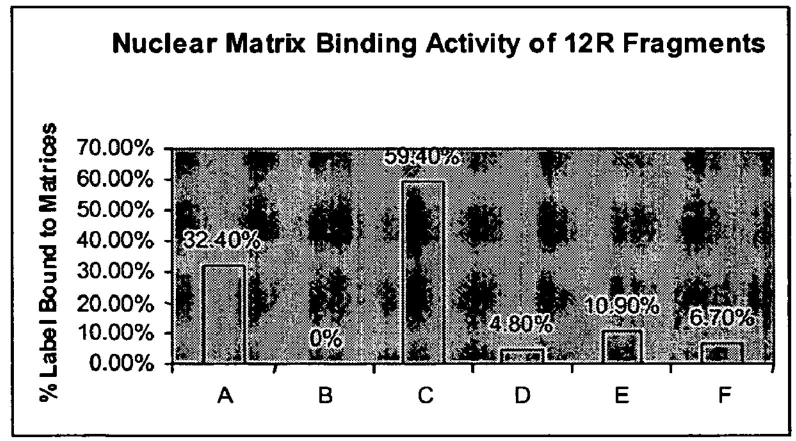
Figure 10:
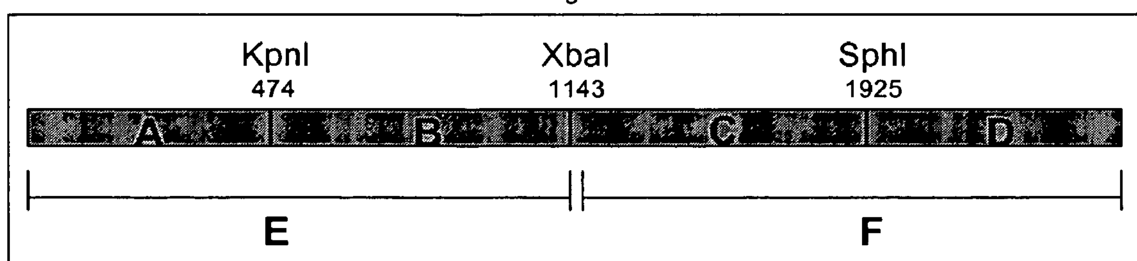

The data shown in FIG. 10 demonstrate that 12R DNA and its fragments have nuclear matrix binding activity. Nuclear matrix binding activity is commonly associated with DNAs comprising matrix attachment regions (MARs). MARs are often closely associated with and frequently flank transcription enhancer and barrier type insulator DNA elements. "Barrier type insulators" can increase gene expression by acting as a barrier that prevents adjacent condensed chromatin from encroaching on, and repressing, an otherwise transcriptionally active gene locus.

Nuclear matrix is the extrachromosomal biochemical fraction prepared from the nuclei of eukaryotic cells. When viewed using microscopy techniques, nuclear matrix appears as an extensively branched net of fibrogranular structures associated with the nuclear membrane and loops of genomic DNA. These loops of DNA may be condensed, associated with chromatin, and presumably transcriptionally repressed or extended and presumably transcriptionally active.

Nuclear matrix from C463A Sp2/0 murine myeloma cells was prepared and nuclear matrix binding assays were performed using the methods of Yusufzai and Felsenfeld to identify DNAs containing MARs elements (Yusufzai and Felsenfeld, *Proc Natl Acad Sci U.S.A.*, 101:8620-8624 (2004)). The 6R and 12R DNAs were fluorescently labeled for these experiments. Restriction fragments of 12R designated A (SEQ ID NO: 3), B (SEQ ID NO: 4), C (SEQ ID NO: 5), D (SEQ ID NO: 6), E (SEQ ID NO: 7), and F (SEQ ID NO: 8) were also prepared and fluorescently labeledusing standard methods. Eukaryotic DNA containing an IgH intronic enhancer element known to contain MARs was also radiolabeled and used as a positive control.

Fluorescently labeled DNAs were then incubated with nuclear matrix. Nuclear matrices and any associated DNAs were pelleted by high speed centrifugation. Co-precipitated DNAs containing matrix associating regions were then separated from the nuclear matrix proteins by proteinase K digestion followed by standard phenol/chloroform extraction and ethanol precipitation. Precipitated DNA pellets were then resuspended in buffer and resolved on 1.2% agarose gel and fluorescent bands werequantified.

Nuclear matrix binding assay data shown in FIG. 11 clearly indicates that the 12R DNA as well as the A and C fragments of 12R, contain MARs DNA elements that typically flank transcription enhancer and barrier type insulator DNA elements. This result also suggests that the B and D fragments flanking the A and C fragments may also be important in gene expression as sequences flanking MARs are often transcriptionally active and play important roles in gene expression. Additionally, these data suggest that the larger E and F fragments encompassing the MARs containing A and C fragments may play important roles in gene expression. Together, these result indicate that 12R, restriction fragment A, restriction fragment B, restriction fragment C, restriction fragment D, restriction fragment E and restriction fragment F contain core DNA elements important in gene expression. These core DNA elements may be capable of functioning as enhancers or barrier type insulators to increase the transcription, and ultimately expression, of genes to which these elements are linked or functioning in other ways to modulate gene expression.

EXAMPLE 7

Identification of Core 6R and 12R DNA Elements that Increase Recombinant Gene Expression Core DNA elements that increase recombinant gene expression and are present in the 6R and 12R DNAs can be readily identified. First, fragments of the 6R and 12R DNAs will be generated and subcloned. 6R and 12R DNA fragments can be generated using techniques such as restriction enzyme digestion or PCR. Such fragments may include 6R and 12R DNA with 5', 3' or internally located deletions of any size. Fragments may also include 6R and 12R DNAs with 5', 3' or internally located insertions or substitutions. When necessary, techniques well known to those skilled in the art can be used to eliminate 5' or 3' DNA overhangs from fragments such as restriction fragments.

Individual, subcloned 6R and 12R DNA fragments will then be linked to a reporter gene in a nucleic acid construct. p2106-DVBase-ZsGreen (DV-BASE), described above, is an example of a nucleic acid construct in which 6R and 12R DNA fragments can be linked to a reporter gene. Fragments may be linked 5' or 3' to the reporter gene in any orientation, alone or in combination, and be inserted at varying distances from the reporter gene to address positional effects. The reporter gene may be any gene expressing a protein.

Reporter gene expression from the reporter nucleic acid construct containing 6R or 12R DNA fragments and the parent construct lacking these fragments will then be measured. Gene expression from the reporter nucleic acid construct can be accomplished in vivo, for example, by transfecting appropriate cells with the construct. If p2106-DVBase-ZsGreen (DV-BASE) type constructs are used CHOK1-SV cells can be transfected. Stable transfectants will be most suitable for the identification of core 6R and 12R DNA elements that increase recombinant gene expression, but transient transfection may also be appropriate.

Expression of the reporter gene may then be monitored by assaying reporter gene encoded protein expression or activity. For p2106-DVBase-ZsGreen (DV-BASE) type constructs, GFP expression can be monitored using standard fluorescence based assays. In some instances reporter gene transcript levels may be assayed and used as a proxy for reporter gene protein expression.

6R and 12R DNA fragments containing core elements capable of increasing reporter gene expression will produce higher levels of expression than parent reporter nucleic acid constructs lacking these fragments. Such core DNA elements may be used interchangeably with SEQ ID NO: 1 or SEQ ID NO: 2 in the compositions, methods, and cells described herein. Such core elements may increase expression through a variety of different mechanisms and may be, for example, transcription enhancer elements or barrier type insulator elements.

The present invention now being fully described, it will be apparent to one of ordinary skill in the art that many changes and modifications can be made thereto without departing from the spirit or scope of the appended claims.

The invention claimed is:

1. An isolated DNA comprising a nucleic acid having the sequence shown SEQ ID NO: 1 and SEQ ID NO: 2.

2. An isolated DNA consisting essentially of a nucleic acid having the sequence shown SEQ ID NO: 1 or 2.

3. An isolated DNA comprising a nucleic acid having the sequence shown in SEQ ID NO: 1 or 2 operably linked to a recombinant DNA encoding a peptide chain.

4. The DNA of claim 3 wherein the recombinant DNA is a cDNA.

5. The DNA of claim 3 wherein the nucleic acid having the sequence shown in SEQ ID NO: 1 is operably linked on the 3' side of the recombinant DNA encoding a peptide chain.

6. The DNA of claim 5 further comprising a DNA encoding a glutamine synthetase.

7. The DNA of claim 3 wherein the peptide chain is an antibody fragment.

8. The DNA of claim 3 wherein the nucleic acid having the sequence shown in SEQ ID NO: 2 is operably linked on the 5' side of the recombinant DNA encoding a peptide chain.

9. The DNA of claim 8 further comprising a DNA encoding a glutamine synthetase.

10. The DNA of claim 8 wherein the peptide chain is an antibody fragment.

11. An isolated DNA comprising a nucleic acid having the sequence shown in SEQ ID NO: 1 and SEQ ID NO: 2 operably linked to a recombinant DNA encoding a peptide chain.

12. The DNA of claim 11 wherein the recombinant DNA is a cDNA.

13. The DNA of claim 11 wherein the nucleic acid having the sequence shown in SEQ ID NO: 1 is operably linked on the 3' side of the recombinant DNA and the nucleic acid having the sequence shown in SEQ ID NO: 2 is operably linked on the 5' side of the recombinant DNA.

14. The DNA of claim 13 further comprising a DNA encoding a glutamine synthetase.

15. The DNA of claim 14 wherein the peptide chain is an antibody fragment.

16. A method of producing a peptide chain expression host cell comprising the steps of:

a) providing a eukaryotic cell;

b) introducing into the cell a DNA comprising a nucleic acid having the sequence shown in SEQ ID NO: 1 or 2 or both SEQ ID NO: 1 and SEQ ID NO: 2; and c) identifying a cell in which the introduced DNA is operably linked to a DNA encoding a peptide chain.

17. A method of producing a peptide chain expression host cell comprising the steps of:

a) providing a eukaryotic cell; and b) introducing into the cell a DNA comprising a nucleic acid having the sequence shown in SEQ ID NO: 1 or 2 SEQ ID NO: 1 and 2 operably linked to a DNA encoding a peptide chain.

18. A method of producing a peptide chain expression host cell comprising the steps of:

a) providing a eukaryotic cell containing a nucleic acid having the sequence shown in SEQ ID NO: 1 or 2 or SEQ ID NO: 1 and SEQ ID NO: 2;

b) introducing into the cell a DNA encoding a peptide chain; and c) identifying a cell in which the introduced DNA is operably linked to SEQ ID NO: 1 or 2 or SEQ ID NO: 1 and 2.

19. A cell produced by the method of claim 16, 17, or 18.

20. A method of producing a peptide chain comprising culturing the cell of claim 19.

* * * * *

UNITED STATES PATENT AND TRADEMARK OFFICE
CERTIFICATE OF CORRECTION

PATENT NO. : 7,498,150 B2
APPLICATION NO. : 11/503103
DATED : March 3, 2009
INVENTOR(S) : Nelson et al.

It is certified that error appears in the above-identified patent and that said Letters Patent is hereby corrected as shown below:

Column 27, line 35 through Column 28, line 65, please replace the claims with the attached corrected claims:

Col. 27 line 35-36

1. An isolated DNA comprising a nucleic acid having the sequence shown SEQ ID NO: 1 and SEQ ID NO: 2.

Col. 27 line 37-38

2. An isolated DNA consisting essentially of a nucleic acid having the sequence shown SEQ ID NO: 1 or 2.

Col. 27 line 39-42

3. An isolated DNA comprising a nucleic acid having the sequence shown in SEQ ID NO: 1 or 2 operably linked to a recombinant DNA encoding a peptide chain.

Col. 27 line 43

4. The DNA of claim 3 wherein the recombinant DNA is a cDNA.

Col. 27 line 44-47

5. The DNA of claim 3 wherein the nucleic acid having the sequence shown in SEQ ID NO: 1 is operably linked on the 3' side of the recombinant DNA encoding a peptide chain.

Col. 27 line 48

6. The DNA of claim 5 further comprising a DNA encoding a glutamine synthetase.

Col. 27 line 49

7. The DNA of claim 3 wherein the peptide chain is an antibody fragment.

Col. 27 line 51-53

8. The DNA of claim 3 wherein the nucleic acid having the sequence shown in SEQ ID NO: 2 is operably linked on the 5' side of the recombinant DNA encoding a peptide chain.

Col. 28 line 46-53

17. A method of producing a peptide chain expression host cell comprising the steps of:

a) providing a eukaryotic cell; and b) introducing into the cell a DNA comprising a nucleic acid having the sequence shown in SEQ ID NO: 1 or 2 or SEQ ID NO: 1 and 2 operably linked to a DNA encoding a peptide chain.

Col. 28 line 54-61

18. A method of producing a peptide chain expression host cell comprising the steps of:

a) providing a eukaryotic cell containing a nucleic acid having the sequence shown in SEQ ID NO: 1 or 2 or SEQ ID NO: 1 and SEQ ID NO: 2;

b) introducing into the cell a DNA encoding a peptide chain; and c) identifying a cell in which the introduced DNA is operably linked to SEQ ID NO: 1 or 2 or SEQ ID NO: 1 and 2.

20. A method of producing a peptide chain comprising culturing the cell of claim 19.

Signed and Sealed this

Sixth Day of April, 2010

David J. Kappos
*Director of the United States Patent and Trademark Office*